(12) United States Patent
Zorlutuna

(10) Patent No.: US 10,910,573 B2
(45) Date of Patent: Feb. 2, 2021

(54) CELL-BASED ELECTROMECHANICAL BIOCOMPUTING

(71) Applicant: The University of Notre Dame du Lac, South Bend, IN (US)

(72) Inventor: Pinar Zorlutuna, South Bend, IN (US)

(73) Assignee: The University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 15/259,887

(22) Filed: Sep. 8, 2016

(65) Prior Publication Data

US 2017/0069860 A1   Mar. 9, 2017

Related U.S. Application Data

(60) Provisional application No. 62/215,367, filed on Sep. 8, 2015.

(51) Int. Cl.

| | | |
|---|---|---|
| *H01L 51/05* | (2006.01) | |
| *G06N 3/063* | (2006.01) | |
| *C12N 5/077* | (2010.01) | |
| *H01L 51/00* | (2006.01) | |
| *G06N 3/00* | (2006.01) | |

(52) U.S. Cl.
CPC ........ *H01L 51/0575* (2013.01); *C12N 5/0656* (2013.01); *C12N 5/0657* (2013.01); *C12N 5/0658* (2013.01); *G06N 3/002* (2013.01); *G06N 3/063* (2013.01); *H01L 51/0093* (2013.01); *C12N 2501/727* (2013.01); *C12N 2501/999* (2013.01); *C12N 2502/1323* (2013.01); *C12N 2502/1329* (2013.01); *C12N 2506/45* (2013.01); *C12N 2533/10* (2013.01); *C12N 2533/52* (2013.01); *C12N 2535/10* (2013.01)

(58) Field of Classification Search
CPC .. H01L 51/0093; H01L 51/0575; G06N 3/002
See application file for complete search history.

(56) References Cited

U.S. PATENT DOCUMENTS

| | | | | |
|---|---|---|---|---|
| 2003/0044802 A1* | 3/2003 | Sayler | ............... | B82Y 10/00 435/6.11 |
| 2006/0020371 A1* | 1/2006 | Ham | ............... | G01R 33/302 700/266 |
| 2008/0293139 A1* | 11/2008 | Watanabe | ............ | C12N 5/0068 435/395 |
| 2013/0274838 A1* | 10/2013 | Entcheva | ............ | A61N 5/0601 607/89 |
| 2014/0129498 A1* | 5/2014 | Bichler | ................. | G06N 3/049 706/25 |

OTHER PUBLICATIONS

Haraguchi, Y. et al. "Electrical Interaction Between Cardiomyocyte Sheets Separated by Non-Cardiomyocyte Sheets in Heterogeneous Tissues." Journal of Tissue Engineering and Regenerative Medicine, vol. 4, issue 4, pp. 291-299. Dec. 11, 2009.*

(Continued)

*Primary Examiner* — Eduardo A Rodela
*Assistant Examiner* — Christopher M Roland
(74) *Attorney, Agent, or Firm* — Greenberg Traurig, LLP

(57) ABSTRACT

A diode and logic gate comprising cells is disclosed. A method of making the diode and logic gate comprising cells is disclosed.

28 Claims, 31 Drawing Sheets

(56) References Cited

OTHER PUBLICATIONS

TerAvest, M. et al. "Bacterial-Based Biocomputing with Cellular Computing Circuits to Sense, Decide, Signal, and Act." Energy and Environmental Science, 2011, 4, 4907-4916.*

Can, U. et al. "Muscle-Cell-Based 'Living Diodes.'" Advanced Biosystems, vol. 1, issue 1-2. Jan. 11, 2017.*

Maleckar, M. et al. "Electronic Coupling Between Human Atrial Myocytes and Fibroblasts Alters Myocyte Excitability and Repolarization." Biophysical Journal, vol. 97, pp. 2179-2190. Oct. 2009.*

Nakano, T. "Biological Computing Based on Living Cells and Cell Communication." 2010 13th International Conference on Network-Based Information Systems, pp. 42-47. (Year: 2010).*

Rother, J. et al. "Crosstalk of Cardiomyocytes and Fibroblasts in Co-Cultures." Open Biol. 5: 150038. May 28, 2015. (Year: 2015).*

Hasirci et al., "Nanobiomaterials: A review of the existing science and technology, and new approaches," Journal of Biomaterials Science, Polymer Edition, 2006; 17(11):1241-68.

Chan et al., "Three-dimensional photopatterning of hydrogels using stereolithography for long-term cell encapsulation," Lab on a Chip—Miniaturisation for Chemistry and Biology, 2010; 10(16):2062-70.

Nikkhah et al, "Directed endothelial cell morphogenesis in micropatterned gelatin methacrylate hydrogels," Biomaterials, 2012; 33(35):9009-18.

Zorlutuna et al, "Microfabricated biomaterials for engineering 3D tissues," Advanced Materials, 2012; 24(14):1782-804.

Gauvin et al, "Microfabrication of complex porous tissue engineering scaffolds using 3D projection stereolithography," Biomaterials. 2012; 33(15):3824-34.

Bajaj et al, "3-D biofabrication using stereolithography for biology and medicine," Conf Proc IEEE Eng Med Biol Soc. 2012, 2012:6805-8.

Jeong et al, "'Living' microvascular stamp for patterning of functional neovessels; Orchestrated control of matrix property and geometry," Advanced Materials, 2012; 24(1):58-63.

Zorlutuna et al, "Nanopatterned collagen tubes for vascular tissue engineering," Journal of Tissue Engineering and Regenerative Medicine, 2008;2(6):373-7.

Zorlutuna et al, "Nanopatterning of collagen scaffolds improve the mechanical properties of tissue engineered vascular grafts," Biomacromolecules, 2009; 10(4):814-21.

Zorlutuna et al, "Both sides nanopatterned tubular collagen scaffolds as tissue-engineered vascular grafts," Journal of Tissue Engineering and Regenerative Medicine, 2010; 4(8):628-37.

Zorlutuna et al, "Stereolithography-Based Hydrogel Microenvironments to Examine Cellular Interactions," Advanced Functional Materials, 2011; 21(19):3642-51.

Bajaj et al, "Patterning the differentiation of C2C12 skeletal myoblasts," Integrative Biology, 2011; 3(9):897-909.

Zorlutuna et al, "Influence of keratocytes and retinal pigment epithelial cells on the mechanical properties of polyester-based tissue engineering micropatterned films," Biomaterials, 2007; 28(24):3489-96.

Zorlutuna et al, "Influence of nanopatterns on endothelial cell adhesion: Enhanced cell retention under shear stress," Acta Biomaterialia, 2009; 5(7):2451-9.

Shin et al, "Carbon-Nanotube-Embedded Hydrogel Sheets for Engineering Cardiac Constructs and Bioactuators," ASC Nano, 2013; 26;7(3):2369-80.

Zhao et al, "Rate-and depth-dependent nanomechanical behavior of individual living Chinese hamster ovary cells probed by atomic force microscopy," Journal of materials research, 2006; 21(8):1906-12.

Palumbo et al, "Direct Investigation of Silver Photodissolution Dynamics and Reversibility in Arsenic Trisulphide Thin Films by Atomic Force Microscopy," Nanotechnology, 2013; 24(12):125706.

Bosse et al, "Multidimensional SPM applied for Nanoscale Conductance Mapping," J Mater. Res. 2013; 28(24):3311-21.

Polomoff et al, "Ferroelectric domain switching dynamics with combined 20 nm and 10 ns resolution," Journal of Materials Science, 2009; 44(19):5189-96.

Bosse et al, "High Speed Friction Microscopy and Nanoscale Friction Coefficient Mapping," Nanotechnology, 2013; submitted.

Huey BD, "AFM and acoustics: Fast, quantitative nanomechanical mapping," Annual Review of Materials Research, 2007; 37:351-85.

Huey et al, "High Speed SPM Applied for Direct Nanoscale Mapping of the Influence of Defects on Ferroelectric Switching Dynamics," Journal of the American Ceramic Society (& cover), 2012; 95(4):1147-62.

Nath et al, "High speed piezoresponse force microscopy: <1 frame per second nanoscale imaging," Applied Physics Letters, 2008; 93:072905.

Cross et al, "Nanomechanical analysis of cells from cancer patients," Nature Nanotechnology, 2007; 2(12):780-3.

Dufrêne YF, "Towards nanomicrobiology using atomic force microscopy," Nature Reviews Microbiology, 2008; 6(9):674-80.

Fletcher et al, "Cell mechanics and the cytoskeleton," Nature, 2010; 463(7280):485-92.

Gavara et al, "Determination of the elastic moduli of thin samples and adherent cells using conical AFM tips," Nature Nanotechnology, 2012; 7(11):733-6.

Madl et al, "A combined optical and atomic force microscope for live cell investigations," Ultramicroscopy, 2006; 106(8-9):645-51.

Silberberg et al, "Mitochondrial displacements in response to nanomechanical forces," Journal of Molecular Recognition, 2008; 21(1):30-6.

Wang et al, "Digital biosensors with built-in logic for biomedical applications—biosensors based on a biocomputing concept," Anal Bioanal Chem, 2010; 398(20464382):1591-603.

Zavalov et al, "Enzyme-based logic: Or gate with double-sigmoid filter response," Journal of Physical Chemistry B, 2012;116(32):9683-9.

Auslander et al, "Programmable single-cell mammalian biocomputers," Nature, 2012; 486(7405):123-7.

Moon et al, "Genetic programs constructed from layered logic gates in single cells," Nature, 2012; 491(7423):249-53.

Sanders et al, "Chip-based microsystems for genomic and proteomic analysis," TrAC—Trends in Analytical Chemistry, 2000; 19(6):364-78.

Feinerman et al, "Reliable neuronal logic devices from patterned hippocampal cultures," Nature Physics, 2008; 4(12):967-73.

Kohl et al, "Electrical coupling of fibroblasts and myocytes: relevance for cardiac propagation," Journal of electrocardiology, 2005; 38(4 Suppl):45-50.

Miragoli et al, "Electrotonic modulation of cardiac impulse conduction by myofibroblasts," Circulation research, 2006; 98(6):801-10.

Gaudesius et al, "Coupling of cardiac electrical activity over extended distances by fibroblasts of cardiac origin," Circulation research, 2003; 93(5):421-8.

Camelliti et al, "Fibroblast network in rabbit sinoatrial node: structural and functional identification of homogeneous and heterogeneous cell coupling," Circulation research, 2004; 94(6):828-35.

Xie et al, "Effects of fibroblast-myocyte coupling on cardiac conduction and vulnerability to reentry: A computational study," Heart rhythm: the official journal of the Heart Rhythm Society, 2009; 6(11):1641-9.

Jacquemet et al, "Modelling cardiac fibroblasts: interactions with myocytes and their impact on impulse propagation," Europace : European pacing, arrhythmias, and cardiac electrophysiology, 2007; 9 Suppl 6:37.

Haraguchi et al, "Electrical interaction between cardiomyocyte sheets separated by non-cardiomyocyte sheets in heterogeneous tissues," Journal of tissue engineering and regenerative medicine, 2010; 4(4):291-9.

Balse et al, "Dynamic of ion channel expression at the plasma membrane of cardiomyocytes," Physiological Reviews, 2012; 92(3):1317-58.

Camelliti et al, "Structural and functional characterisation of cardiac fibroblasts," Cardiovascular Research, 2005; 65(1):40-51.

(56) References Cited

OTHER PUBLICATIONS

Sachse et al, "Electrophysiological modeling of fibroblasts and their interaction with myocytes," Annals of Biomedical Engineering, 2008; 36(1):41-56.

Feld et al, "Electrophysiological modulation of cardiomyocytic tissue by transfected fibroblasts expressing potassium channels: A novel strategy to manipulate excitability," Circulation, 2002; 105(4):522-9.

Walsh et al, "Neonatal rat cardiac fibroblasts express three types of voltagegated K+ channels: Regulation of a transient outward current by protein kinase C," American Journal of Physiology—Heart and Circulatory Physiology, 2008; 294(2):H1010-H7.

Kohl et al, "Mechanosensitive fibroblasts in the sino-atrial node region of rat heart: Interaction with cardiomyocytes and possible role," Experimental Physiology, 1994; 79(6):943-56.

Tang et al, "How far cardiac cells can see each other mechanically," Soft Matter, 2011; 7(13):6151-8.

Zhang et al, "Cross talk between cardiac myocytes and fibroblasts: From multiscale investigative approaches to mechanisms and functional consequences," American Journal of Physiology—Heart and Circulatory Physiology, 2012; 303(12):H1385-H96.

Cherry et al, "Realistic cardiac electrophysiology modelling: Are we just a heartbeat away?," Journal of Physiology, 2010; 588(15)2689.

Karma A, "Spiral breakup in model equations of action potential propagation in cardiac tissue," Physical Review Letters, 1993; 71(7):1103-6.

He et al, "Long-distance intercellular connectivity between cardiomyocytes and cardiofibroblasts mediated by membrane nanotubes," Cardiovascular Research, 2011; 92(1):39-47.

McSpadden et al, "Electrotonic loading of anisotropic cardiac monolayers by unexcitable cells depends on connexin type and expression level," American journal of physiology Cell physiology, 2009; 297(2):51.

Takens-Kwak et al, "Mechanism of heptanol-induced uncoupling of cardiac gap junctions: A perforated patch-clamp study," American Journal of Physiology—Cell Physiology, 1992; 262(6 31-6):C1531-C8.

Azeloglu et al, "Cross-bridge cycling gives rise to spatiotemporal heterogeneity of dynamic subcellular mechanics in cardiac myocytes probed with atomic force microscopy," Am J Physiol Heart Circ Physiol, 2010; 298:H853-60.

Chang et al, "Characterization of the Mechanodynamic Response of Cardiomyocytes with Atomic Force Microscopy," Analytical Chemistry, 2013; 85:1395-40.

Liu et al, "Atomic Force Mechanobiology of Pluripotent Stem Cell-Derived Cardiomyocytes," PLOS One, 2012; 7(5):e37559-65.

Liu et al, "In situ mechanical analysis of cardiomyocytes at nano scales," Nanoscale, 2012; 4:99-102.

Verma et al, "Scanning probe microscopy method for nanosuspension stabilizer selection," Langmuir, 2009; 25(21)12481-7.

Zhao et al, "Ultra sharp and high aspect ratio carbon nanotube AFM probes for enhanced surface potential imaging," Nanotechnology, 2008; 19(23):235704-10.

\* cited by examiner

CELL-BASED ELECTROMECHANICAL BIOCOMPUTING

CROSS-REFERENCE TO RELATED APPLICATIONS

This application claims the benefit of, and priority to, U.S. Provisional Application Ser. No. 62/215,367, filed Sep. 8, 2015, which is incorporated herein in its entirety.

STATEMENT REGARDING FEDERALLY SPONSORED RESEARCH OR DEVELOPMENT

This invention was made with Government support under grant no. 1403546, awarded by the National Science Foundation. The U.S. government has certain rights in the invention.

BACKGROUND

Field

The present disclosure relates at least in part to a diode comprising at least one cell, a logic gate comprising at least one cell, and a circuit comprising at least one cell. The disclosure additionally relates to methods of fabrication of a diode comprising at least one cell, a logic gate comprising at least one cell, and a circuit comprising at least one cell.

Description of Related Art

Biocomputing is a developing field, which has recently emerged around the idea of using biomolecular systems for information processing. Initially limited to single logic-gated chemical computing, over the years it has introduced the complexity of using multiple logic gates to form circuits mostly using cell-derived biomacromolecules (such as enzyme complexes), and more recently cells themselves through genetic manipulations that alter their gene expression profile, to achieve biological information processing. In the current paradigm of biocomputing, mostly single cells (either bacteria or single mammalian cells) are used, and the information processing is done at the gene or protein level where the information is processed through differential gene and protein expression usually in the end controlling the production of certain enzymes. The input is introduced and output is read as chemical signals.

In addition to chemical signals, some cells are also responsive to electrical signals. More recently, rat hippocampal neuron cells were used to produce circuit elements. These circuit elements were built by exploiting the differential electrical response of neuronal cell networks depending on their connection density in order to study neuronal information processing. Under normal culturing conditions, and upon reaching a certain density, neuron cell networks fire signal bursts both spontaneously and upon electrical stimulation. By confining the cells to defined geometries, it was possible to create thresholds. This was achieved by controlling the degree of synapse formation between the neurons and by using chemical molecules to block certain regions of the patterned cells. However, logic gate functionality for such patterned neuron cultures is still dependent on local chemical concentrations that block the signal propagation at certain locations.

SUMMARY

In one embodiment, the present disclosure provides a diode comprising at least one excitable cell, at least one non-excitable cell, and a first connector and a second connector. In some configurations, the first connector can be electrically connected to the at least one excitable cell, the second connector can be electrically connected to the at least one non-excitable cell, and the at least one excitable cell and the at least one non-excitable cell can be electrically connected.

In one embodiment, the present disclosure provides a logic gate comprising at least one first and at least one second excitable cell, at least one non-excitable cell, a first connector, a second connector, and a third connector. In some configurations, the at least one first excitable cell can be electrically connected to the at least one non-excitable cell, the at least one second excitable cell can be electrically connected to the at least one non-excitable cell, the first connector can be electrically connected to the at least one first excitable cell, the second connector can be electrically connected to the at least one second excitable cell, and the third connector can be electrically connected to the at least one non-excitable cell.

In one embodiment, the present disclosure provides a logic gate comprising at least one first and at least one second excitable cell, at least one non-excitable cell, a first connector, a second connector, and a third connector. In some configurations, the at least one first excitable cell can be electrically connected to the at least one non-excitable cell, the at least one second excitable cell can be electrically connected to the at least one non-excitable cell, the first connector can be electrically connected to the at least one first excitable cell, the second connector can be electrically connected to the at least one second excitable cell, and the third connector can be electrically connected to the at least one non-excitable cell.

DETAILED DESCRIPTION

Figure 1:
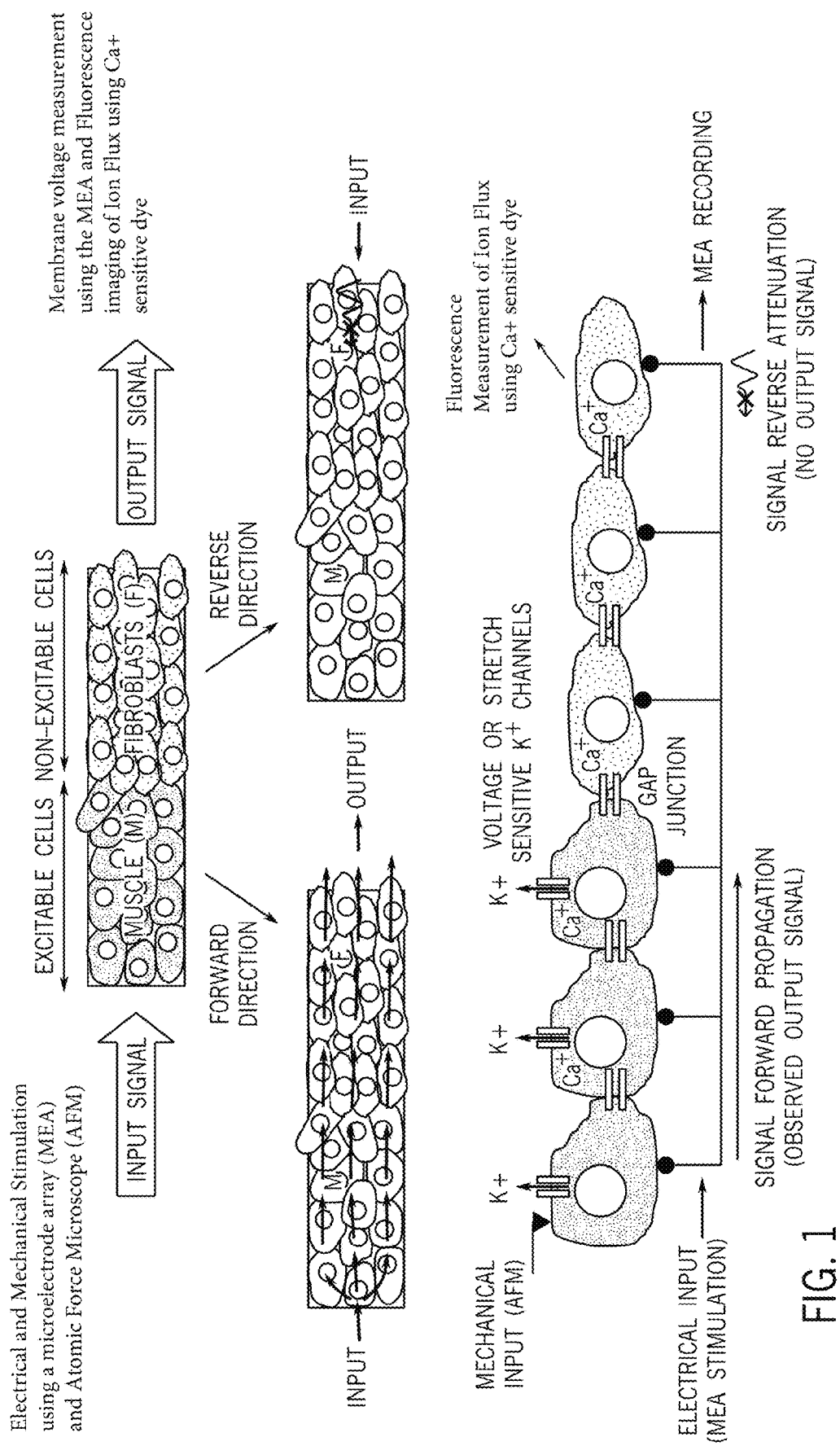
FIG. 1. Schematic overview of cell-based signal processing

The present disclosure is based, at least in part, on the observation that living cells can carry both electrical and mechanical signals, and can be arranged to do so in a directional manner.

Accordingly, disclosed herein are circuit elements comprising at least two cell types and methods of using such circuit elements to create biocomputing devices.

Cell

The term "cell" refers to the basic structural and biological unit of all living organisms. Cells generally comprise cytoplasm enclosed in a membrane; both the cytoplasm and the membrane can comprise many other types of molecules, which can be referred to as biomolecules, including proteins, protein complexes and fatty acids. Cells can differentiate into a variety of cell types; one cell type can have different features and subcellular structures, and a different function within a multicellular organism, from another cell type. Cells of almost all cell types are electrically charged, with the interior of the cell held at a negative voltage relative to the exterior of the cell. This electrical charge is known as the "membrane potential" of the cell, and is usually between about −20 mV and −80 mV.

In a multicellular organism, cells generally interact with, and are physically, mechanically, or electrically attached to other cells of that same multicellular organism. Although cells are usually thought of as discrete units, many cell types comprise "gap junctions." Gap junctions are intercellular connections, which can directly connect the cytoplasm of two cells. Gap junctions can allow electrical or metabolic connection between the cells which the gap junction connects. Two cells can be connected by multiple gap junctions, and one cell can be connected to more than one other cell by gap junctions.

There are many ways to categorize cell types; one useful distinction is whether cells are of an "excitable" or a "non-excitable" cell type. A cell is "excitable" if it is capable of producing an action potential ("AP"), which is a rapid and significant change in the membrane potential of the cell. In a multicellular organism, action potentials are required for some types of cell-to-cell communication, for example in the nervous system and in muscles. Action potentials can be propagated across regions within one cell's membrane, or across cells. Excitable cells include, but are not limited to, neurons, muscle cells (myocytes), and endocrine cells.

Axons (a type of neuron) and cardiomyocytes (heart muscle cells, or cardiac muscle cells) are especially well-studied, and therefore well-understood, types of excitable cells. Cardiac muscle cells, being excitable, can fire action potentials through their voltage-sensitive and stretch-sensitive ion channels upon external electrical or mechanical stimulation. They can actively propagate an input signal via their cell-cell connections (i.e. gap junctions and adherens junctions).

Non-excitable cells are not capable of producing an action potential, because they lack the subcellular structures (i.e., voltage-gated channels) necessary to do so. Many cell types are non-excitable; fibroblasts, epithelial cells, blood cells, adipocyte cells, and stem cells are usually non-excitable cell types. Non-excitable cells cannot propagate a signal coming directly to their membrane from an external source, but they can couple with neighboring cells through cell-cell junctions and can thus passively relay an electrical (via gap junctions) or mechanical (via adherens junctions) signal up to a certain distance.

Muscle cells can propagate a signal to other muscle cells, much like neurons. Furthermore, the excitable muscle cells of the heart tissue can electrically couple with non-excitable cells from the heart wall, the majority of which is composed of fibroblasts. Even though fibroblast cells are not excitable and cannot initiate an action potential like muscle cells, interestingly they can propagate the electrical signal passively. The degree of heart muscle cell-fibroblast cell coupling is relevant to a number of pathological conditions and has been investigated extensively.

Circuit

A "circuit" is a complete electrical network, comprising a closed loop, and which is capable of carrying current. As used herein, a current can be analog or digital; synchronous or asynchronous; series or parallel; integrated; or any other type of circuit known in the art. Circuits can be represented by a circuit diagram. They can be housed on circuit boards, which circuit boards are generally non-conductive substrates; or, in the case of integrated circuits, on semiconductors. Electronic devices can comprise multiple circuits.

Circuits comprise various circuit elements or circuit components. Circuit elements can be connected by connectors. Connectors can be of any material which is capable of carrying current.

Circuits can comprise electrodes, which are any part of a circuit used to make contact with a nonmetallic part of that circuit.

Diodes

Circuits can comprise diodes. A diode is an electrical circuit component that allows directional signal transduction. It is a crucial element of signal processing and a key component of many logic gates. A diode is a circuit element which has a low resistance to the flow of current in one direction, and a high resistance to flow in the other direction. An ideal diode is a switch: it has zero resistance to the flow of current in one direction (open), and infinite resistance to flow in the other direction (closed). Currently, most diodes are made of silicon; but semiconductors of selenium or germanium are also in use.

The current disclosure provides a cell-based diode. The diode comprises at least one excitable cell, and at least one non-excitable cell. In preferred embodiments, the at least one excitable cell is at least one cardiomyocyte, and the at least one non-excitable cell is at least one fibroblast. The at least one excitable cell can be electrically connected to the at least one non-excitable cell. The at least one excitable cell can be mechanically connected to the at least one non-excitable cell. The at least one excitable cell can be both electrically and mechanically connected to the at least one non-excitable cell. Independent of the type of connection between the excitable and non-excitable cells, the excitable and non-excitable cells can be electrically connected to electrodes or other types of connectors, which can themselves be electrically connected to other components in a circuit.

When current is applied to the at least one excitable cell in the diode, the at least one excitable cell can produce an action potential. That action potential can be propagated across other cells in the diode. In some cases, the action potential is propagated across additional excitable cells. In some cases, the action potential is propagated across at least one non-excitable cell. In some cases, the action potential is propagated across both additional excitable cells and across at least one non-excitable cell. The action potential can then be received by an electrode which is electrically connected to the at least one non-excitable cell; therefore current can be transmitted to another component of the circuit.

When current is applied to the at least one non-excitable cell in the diode, no action potential is produced, and no current is transmitted, either within the diode or to other components of the circuit. This ability to propagate current across the diode in only one direction defines this arrangement of excitable and non-excitable cells as a diode.

The at least one excitable cell can be a group of excitable cells. The at least one excitable cell, or the group of excitable cells, can comprise only excitable cells. The at least one excitable cell can comprise a majority of excitable cells and a minority of non-excitable cells. A minority of non-excitable cells in group of excitable cells is defined as an amount of non-excitable cells which does not appreciably alter the electrical or mechanical response of the excitable cells.

The at least one non-excitable cell can be a group of non-excitable cells. Preferably, the at least one non-excitable cell, or the group of non-excitable cells, comprises only non-excitable cells. However, a minority of excitable cells in a group of non-excitable cells is acceptable, provided that the excitable cells do not appreciably alter the electrical or mechanical response of the non-excitable cells.

The at least one excitable cell and the at least one non-excitable cell can be provided in any physical arrangement, as long as the at least one excitable cell and the at least one non-excitable cell are separately, but closely, located. The locations should be close enough that the cells are electrically, mechanically, or both electrically and mechanically connected. The at least one excitable cell and the at least one non-excitable cell can be provided as groups of excitable cells and non-excitable cells, and can be provided in any physical arrangement, as long as the group of excitable cells and the group of non-excitable cells are separately, but closely, located. The locations should be close enough that the groups of cells are electrically, mechanically, or both electrically and mechanically connected. The groups of cells can be arranged in any geometric pattern. In some embodiments, both the groups of excitable cells and non-excitable cells can be arranged in substantially rectangular shapes. In some embodiments, both the groups of excitable cells and non-excitable cells can be arranged in substantially square shapes. In other embodiments, the group of excitable cells can be arranged in one shape, while the group of non-excitable cells can be arranged in a different shape.

In some configurations, the group of excitable cells can be provided in a rectangular shape having a first dimension of about 50 µm, and a second dimension of any dimension between 50 µm to 1000 µm, and being of a thickness of one cell.

In some configurations, the group of non-excitable cells can be provided in a rectangular shape having a first dimension of about 50 µm, and a second dimension of any dimension between 50 µm to 1000 µm, and being of a thickness of one cell.

Figure 7:
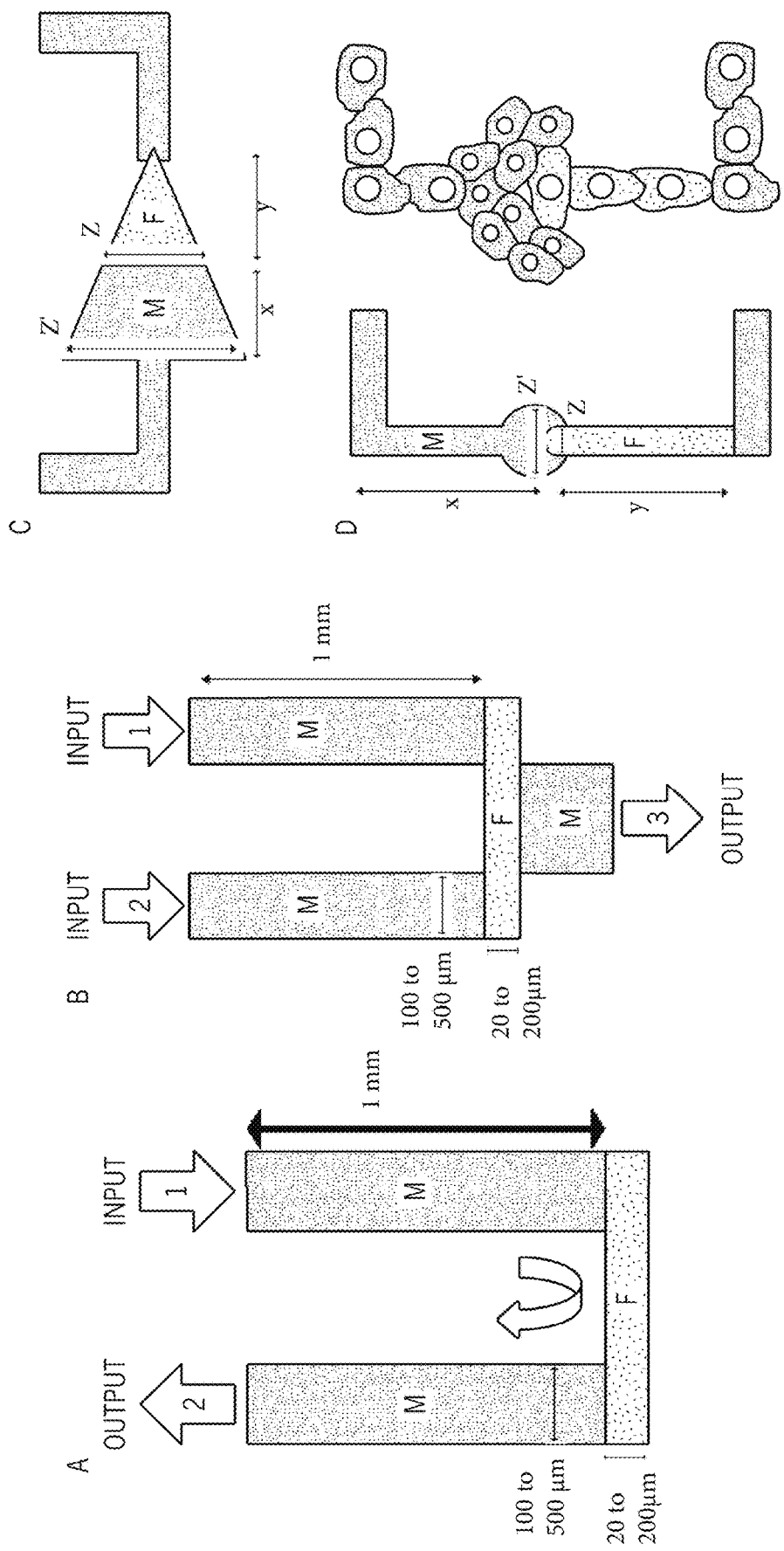
FIG. 7. Logic gate. A) Threshold cell-based logic gate, B) cell-based logical 'AND' gate, C and D) Connection of the cell-based diodes to the cell-based circuits. (M: Muscle Cell, F: Fibroblasts)

In another configuration, as shown in FIG. 7C, a triangular pattern of fibroblasts (ie, non-excitable cells) in a cell-based diode can be used. Since the base of the triangle comprises more fibroblasts than the apex, there are more input signals from that edge compared to the triangle apex where only one or a few fibroblasts are coupled with nearby muscle cells. Therefore, signals relay from the triangular pattern base to the tip, but reverse signals are dampened. In another embodiment, as shown in FIG. 7D, the number of muscle cells coupling with a single fibroblast could be adjusted. Since one side has more muscle cells directly signaling the fibroblast strip than the other side, the signal is again relayed preferentially, specifically from the multiple muscle cell terminal towards the single muscle cell terminal.

Logic Gates

Circuits can comprise logic gates. A logic gate is a component of a circuit, usually a digital circuit. Most logic gates comprise two inputs and one output. There are seven basic logic gates: AND, OR, XOR, NOT, NAND, NOR, and XNOR. Each type of logic gate performs a discrete Boolean function in a circuit—it produces a single logical output after performing a logical operation on one or more logical inputs. For example, an AND gate functions in the same way as a logical "AND" operator. An OR gate behaves like a logical, inclusive "OR". Logic gates are often implemented in circuits by using diodes or transistors, acting as electronic switches. Currently, logic gates are often made from field-effect transistors.

The present disclosure provides a cell-based logic gate. The cells comprised by the logic gate function in place of the diode or transistor in a traditional logic gate. The logic gate can comprise at least one first and at least one second excitable cell, and at least one non-excitable cell. In preferred embodiments, both the at least one first and the at least one second excitable cell can each be at least one cardiomyocyte. In preferred embodiments, the at least one non-excitable cell can be a fibroblast. The at least one first and at least one second excitable cell can be electrically connected to the at least one non-excitable cell. The at least one first and at least one second excitable cell can be mechanically connected to the at least one non-excitable cell. The at least one first and at least one second excitable cell can be both electrically and mechanically connected to the at least one non-excitable cell. The at least one first excitable cell and the at least one second excitable cell can be connected to the non-excitable cell at separate physical locations on the at least one non-excitable cell. Independent of the type of connection or location of the connection between the excitable and non-excitable cells, the excitable and non-excitable cells can be electrically connected to electrodes or other types of connectors, which can themselves be electrically connected to other components in a circuit.

Figure 30:
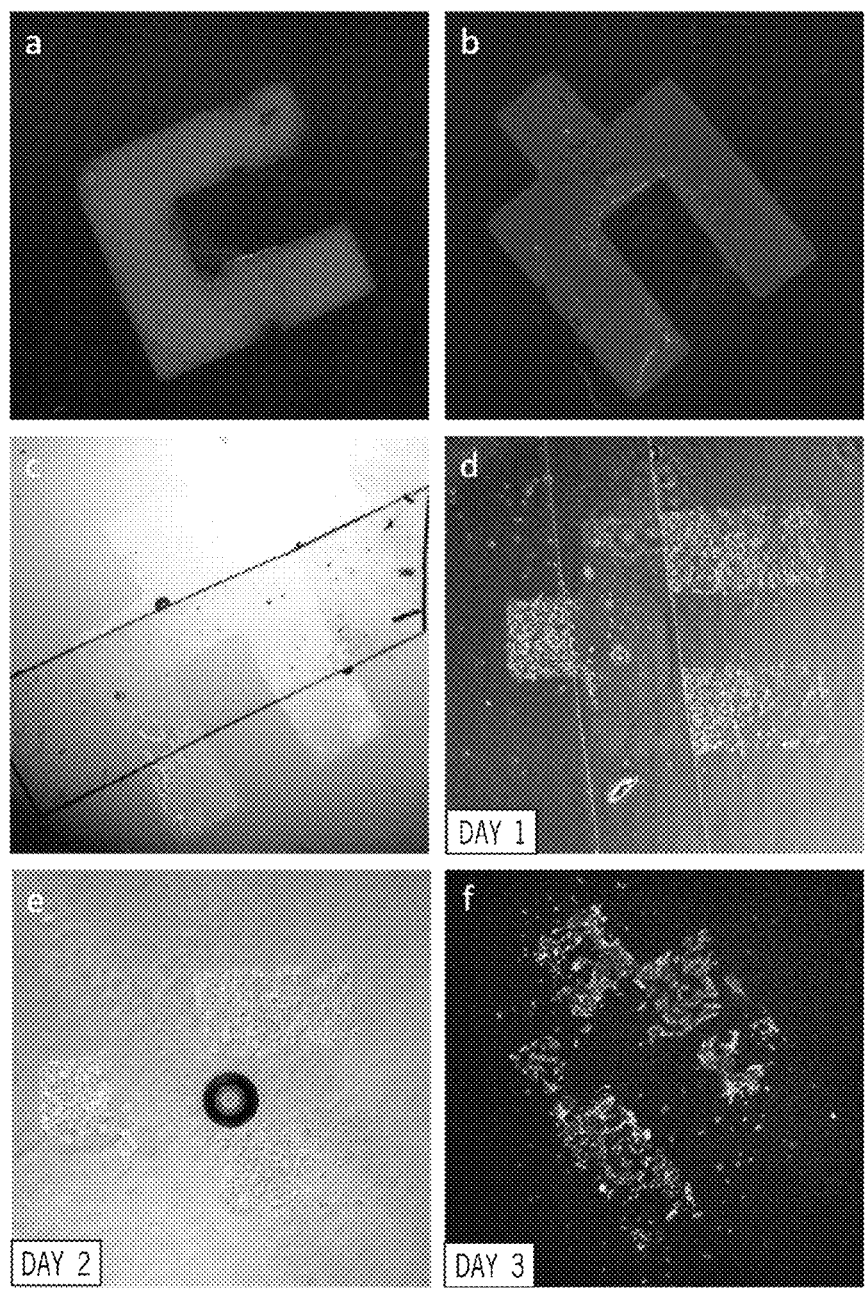
FIG. 30. Patterning logic gates and cell seeding. Fibronectin pattern on the silaned substrate visualized using Alexa-647 tagged fibrinogen (a, b). PMDS covered protein pattern (c). CM enriched cell seeding before (Day 1, d) and after (Day 2, e) PDMS sheet removal. Fluorescence image of Troponin-I (green), Vimentin (red) immunostaining of the cells co-cultured as the logic gate design counter stained for the cell nuclei (blue) (Day 5, c).
Figure 31:
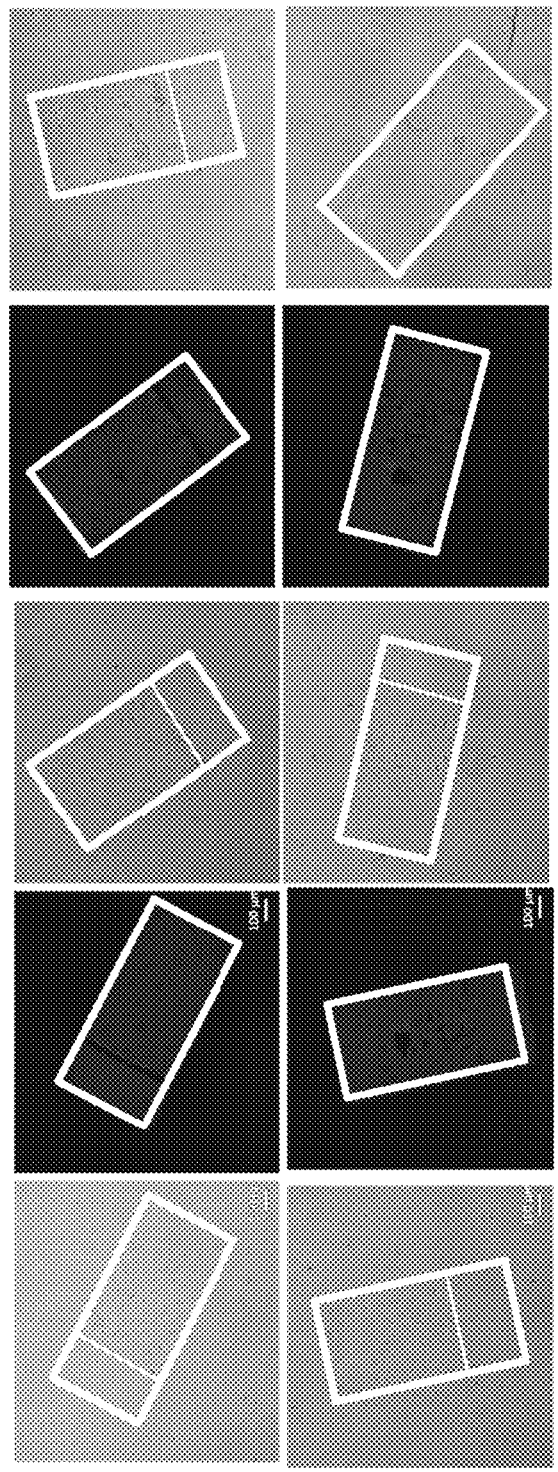
FIG. 31. Detachment of cells along with the protein after Day 3 in culture.
Figure 32:
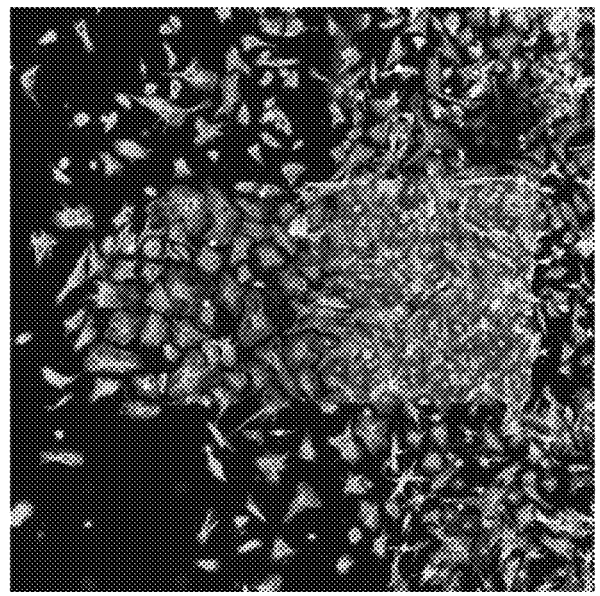
FIG. 32. Fluorescence image of Troponin-I (green) and Vimentin (red) immunostaining of the MCD on a used MEA counter stained for the cell nuclei (blue) (Day 6).
Figure 33:
FIG. 33. Contact angle measurement of silaned substrate (95°, left), new MEA (82°, middle) and used MEA (46°, right) substrates.

One of skill in the art will appreciate that differing arrangements of cells can provide different logic gates. As shown in FIG. 30, for example, it is possible to use the teachings of the present disclosure to create logic gates.

The at least one first and at least one second excitable cell can each be a group of excitable cells. The at least one first and at least one second excitable cell, or the first and second groups of excitable cells, can each comprise only excitable cells. The at least one first and at least one second excitable cell can each comprise a majority of excitable cells and a minority of non-excitable cells. A minority of non-excitable cells in group of excitable cells is defined as an amount of non-excitable cells which would not appreciably alter the electrical or mechanical response of the excitable cells.

The at least one non-excitable cell can be a group of non-excitable cells. Preferably, the at least one non-excitable cell, or the group of non-excitable cells, comprises only non-excitable cells. However, a minority of excitable cells in a group of non-excitable cells is acceptable, provided that the excitable cells would not appreciably alter the electrical or mechanical response of the non-excitable cells.

The at least one first and at least one second excitable cell and the at least one non-excitable cell are separately, but closely, located. The locations should be close enough that the cells are electrically, mechanically, or both electrically and mechanically connected. The at least one first and at least one second excitable cell and the at least one non-excitable cell can be provided as groups of excitable cells and non-excitable cells, and can be provided in any physical arrangement, as long as the group of excitable cells and the group of non-excitable cells are separately, but closely, located. The locations should be close enough that the groups of cells are electrically, mechanically, or both electrically and mechanically connected. The groups of cells can be arranged in any geometric pattern. In some embodiments, both the groups of excitable cells and non-excitable cells can be arranged in substantially rectangular shapes. In some embodiments, both the groups of excitable cells and non-excitable cells can be arranged in substantially square shapes. In other embodiments, the group of excitable cells can be arranged in one shape, while the group of non-excitable cells can be arranged in a different shape.

In some configurations, the first and second groups of excitable cells can be provided in a rectangular shape having a first dimension of about 50 µm, and a second dimension of any dimension between 50 µm to 1000 µm, and being of a thickness of one cell.

In some configurations, the group of non-excitable cells can be provided in a rectangular shape having a first dimension of about 50 µm, and a second dimension of any dimension between 50 µm to 1000 µm, and being of a thickness of one cell.

The arrangement of the at least one first and at least one second excitable cell and the at least one non-excitable cell, relative to each other, determines the function of the logic gate, ie, what type of function the logic gate is capable of implementing. A "U-shaped" arrangement, in which the arms of the U are the first and second groups of excitable cells, and in which the bottom of the U is the group of non-excitable cells, can provide either an AND or OR logic gate. The function of such a logic gate is determined by the size of the area which the group of non-excitable cells occupies, and in particular the thickness of the bottom of the U shape. A wider area of non-excitable cells, causes the logic gate to function as an "AND" gate. A narrower area of non-excitable cells causes the logic gate to function as an "OR" gate.

Figure 18:
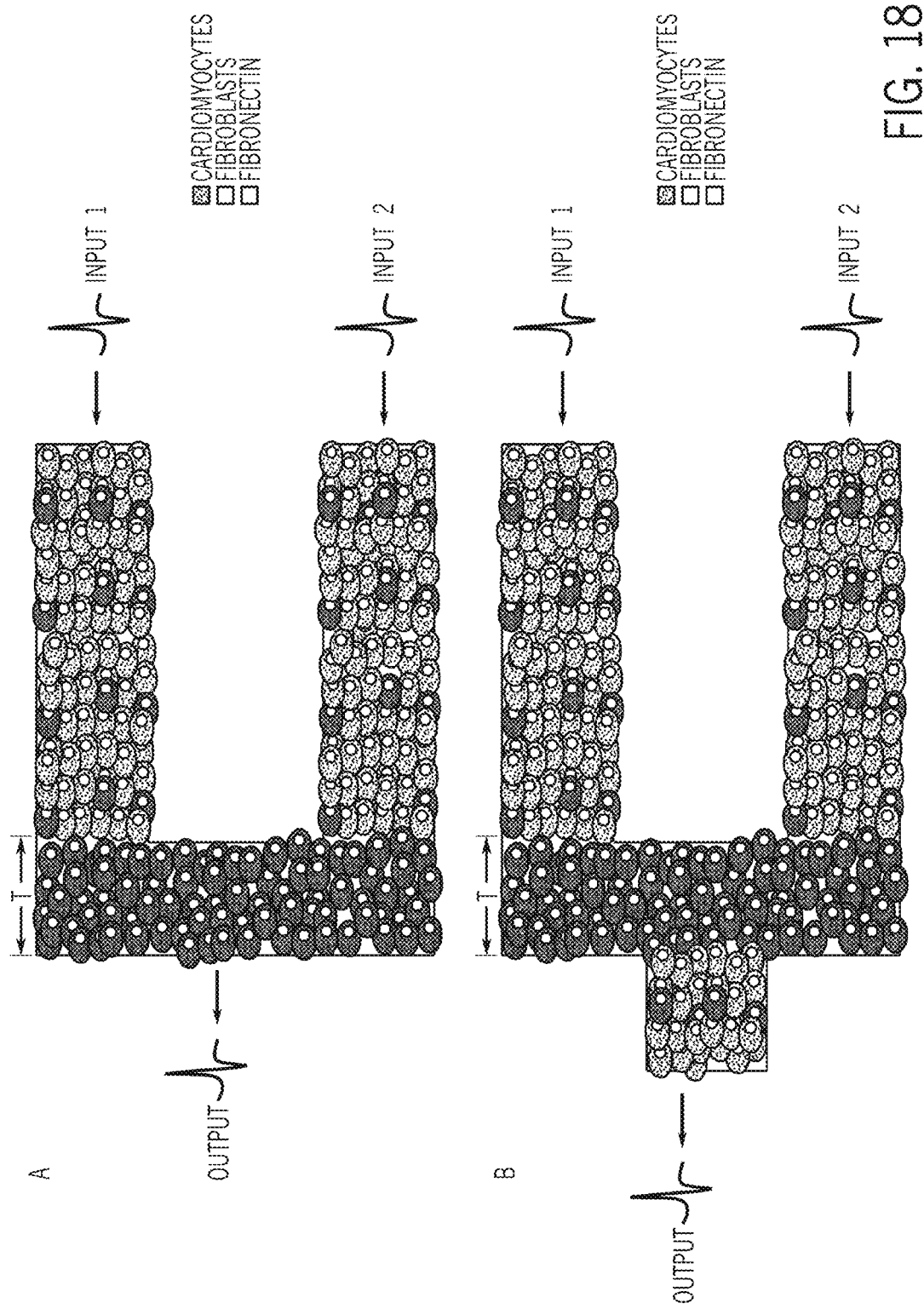
FIG. 18. (a) 'OR' or 'AND' (depending on thickness t) gate design and (b) 'OR' or 'AND' gate with an amplifier at the output.

The logic gate can, optionally, additionally comprise at least one third excitable cell. The at least one third excitable cell can be a group of excitable cells. The at least a third excitable cell can be positioned separately from the at least one first and at least one second excitable cell on the logic gate. In a preferred embodiment, two groups of excitable cells form the arms of a U, the bottom of which is formed from a group of non-excitable cells; and the third group of excitable cells is positioned opposite the bottom of the U from the two groups of excitable cells. FIG. 18 shows a cartoon representation of such a preferred embodiment. Such an architecture for a logic gate allows the third group of excitable cells to receive an action potential from the non-excitable cells, if that action potential is transmitted across the non-excitable cells.

The at least one third excitable cell and the at least one non-excitable cell are separately, but closely, located. The locations should be close enough that the cells are electrically, mechanically, or both electrically and mechanically connected. The at least one third excitable cell and the at least one non-excitable cell can be provided as groups of excitable cells and non-excitable cells, and can be provided in any physical arrangement, as long as the group of excitable cells and the group of non-excitable cells are separately, but closely, located. The locations should be close enough that the groups of cells are electrically, mechanically, or both electrically and mechanically connected. The groups of cells can be arranged in any geometric pattern. In some embodiments, both the groups of excitable cells and non-excitable cells can be arranged in substantially rectangular shapes. In some embodiments, both the groups of excitable cells and non-excitable cells can be arranged in substantially square shapes. In other embodiments, the group of excitable cells can be arranged in one shape, while the group of non-excitable cells can be arranged in a different shape.

In all cases, the first, second, and optional third groups of excitable cells can be electrically connected to other parts of a circuit. In the case of the logic gate comprising only a first and second excitable cell, the non-excitable cell or cells can be electrically connected to other parts of a circuit.

Types of Connections

In embodiments of the present disclosure, elements in a circuit can be connected electrically, mechanically, or both electrically and mechanically ("electromechanically").

Two elements which are electrically connected are connected in a way that allows electric charge (current) to flow between the first element and the second element. In a traditional circuit, a power source can be electrically connected to, for example, a connector; that connector can additionally be electrically connected to, for example, a diode. An electrical connection is a connection between two components of a circuit, including connections between connectors and other types of circuit elements. An electrical connection does not require that two circuit elements be in physical contact, so long as current can flow between those two circuit elements.

As described herein, one or more cells can be electrically connected to connectors, to other cells, or to circuit elements. Such an electrical connection is not dependent on any particular type of physical connection between the one or more cells and the connector, other cells, or circuit elements; but rather on the ability for electric charge to flow from the one or more cells and to the connector, other cells, or circuit elements.

Cells can be connected to one another electrically (eg, via gap junctions) or mechanically (eg, via aherens junctions). When referring specifically to an electrical connection between cells, an electrical connection can be referred to as an "electrotonic coupling," and two or more cells so connected can be referred to as "electronically coupled."

Mechanically connected elements are connected in a way that allows a mechanical stimulus to flow between the two elements. For example, cardiac muscle cells and fibroblasts respond to mechanical stimulation in a similar way. Stretch or shear loading results in excitatory responses in cardiac muscle cells by the aid of stretch activated ion channels, evoking action potentials through a pathway known as mechano-electric feedback. The cardiac muscle cells can be excited to beat solely using a mechanical probe to stimulate a resting (unexcited) cardiac muscle cell to fire an action potential and propagate the beating to the neighboring cells, one mechanism of the efficacy of Cardiopulmonary Resuscitation (CPR). On the other hand, a fibroblast can mechanically couple with cardiac muscle cells, and other fibroblasts, via cell-cell adherens junctions. These junctions are formed via transmembrane proteins called cadherin, which link the intracellular actin and intermediate filaments and thereby facilitate transmission of cytoskeletal tension. Therefore, the similar asymmetrical signal transduction that exploits the differences between the non-excitable and excitable cells upon electrical stimulation can also be leveraged to create directional mechanical signal transduction.

As shown in FIG. 1, in the forward direction, upon electrical or mechanical input using Microelectrode Arrays (MEA) or an Atomic Force Microscope (AFM) probe, respectively, the excitable cells (e.g. muscle cells (M)) would be excited and propagate the input signal. This signal could pass through the non-excitable cells via cell-cell connections that allow ion flux between two adjacent cells (e.g. gap junctions) up to a certain distance, and be detected in the output as mechanical or electrical signals. In the reverse direction, the non-excitable cells (e.g. fibroblasts (F)) could not be excited upon the same magnitude of electrical or mechanical stimulation since they lack the proper ion channels on their membranes, thus the signal could not be propagated, and there would be no detectable output signal.

Methods of Fabricating

Microcontact printing is a well-established method of controlling the cell organization and cell patterning on surfaces. Micropatterning of the exitable cells and non-excitable cells in a controlled manner can result in solely electromechanical information processing without the need for blockers, other chemicals, or altering the gene expression of the cells. Also, the ratio of the excitable cells to non-excitable cells, and the relative ratio of contacting cell types at junctions can be adjusted to generate a desired directional information flow.

Traditional microprinting techniques were found to have significant drawbacks in the current methods, however, because two different cell types are used. Specifically, non-specific cell attachment to the substrate was observed, leading to inappropriate placement of either or both of the excitable or non-excitable cells. Additionally, some cells adhered on top of other cells, rather than onto the substrate, causing detachment or interfering with contractile or conductive properties of the desired cell types.

Accordingly, disclosed herein is a method of stencil-based micropatterning of cells. The method is based, at least in part, on the observation that non-excitable cells are able to proliferate on a micropatterning substrate, but excitable cells do not share that property.

The method of micropatterning cells comprises providing a substrate comprising a protein micropattern. The protein micropattern can be created by any method known to one of skill in the art. For example, the substrate can be silicon. The protein which is micropatterned can be fibronectin. The protein micropattern can be of any shape, including but not limited to squares, rectangles, U-shapes, or any other shape desirable for use in a cells-based diode or cell-based logic gate. The protein micropattern can be of any size. The length of a group of excitable cells in a protein micropattern can be at least about 50 μm (x, in FIG. 3a). The length of a group of non-excitable cells in a protein micropattern can be at least about 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 225 μm, 250 μm, 275 μm, 300 μm, 325 μm, 350 μm, 375 μm, 400 μm, 425 μm, 450 μm, 475 μm, or 500 μm (y, in FIG. 3a). Protein micropatterns can have size ratios of 1x:1y to 1x:10y. Protein micropatterns can have a height of 50 μm to 200 μm (z, in FIG. 3a).

Then a portion of the protein micropattern can be covered, and a solution comprising both at least one excitable cell and at least one non-excitable cell can be applied to the uncovered portion of the protein micropattern. The shape and relative size of both the covered and uncovered portions of the protein micropattern can be of any dimensions or arrangement. The cells in the solution comprising both at least one excitable cell and at least one non-excitable cell should be provided as about 19%+/−1% non-excitable cells, and 81%+/−1% excitable cells. In a preferred embodiment, the excitable cell can be a cardiomyocyte, and the non-excitable cell can be a fibroblast. The cells in the solution can be allowed to adhere to the uncovered portion of the protein micropattern; the portion which is contacted with the solution (ie, which is left uncovered) is the portion of the protein micropattern which is populated by a group of excitable cells.

The solution comprising both at least one excitable cell and at least one non-excitable cell can be removed from the protein micropattern. The covering can then be removed from the first portion of the protein micropattern, and the non-excitable cells adhered to the protein micropattern can be allowed to proliferate, thereby populating the first portion of the protein micropattern.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification can, but do not necessarily, all refer to the same embodiment.

Furthermore, the described features, structures, or characteristics of the invention may be combined in any suitable manner in one or more embodiments. In the description, numerous specific details are provided. One skilled in the relevant art will recognize, however, that the invention can be practiced without one or more of the specific details, or with other methods, components, materials, and so forth. In other instances, structures, materials, or operations that are known in the art are not shown or described in detail to avoid obscuring aspects of the invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "about" is used herein to mean a value − or +20% of a given numerical value. Thus, "about 60%" means a value of between 60−(20% of 60) and 60+(20% of 60) (i.e., between 48 and 70).

As used herein, the terms "coupled", "linked", "connected" and other like terms are used interchangeably. These terms refer to the joining together of two more elements or components by whatever means, including electrical connection, mechanical connection, or electromechanical connection.

EXAMPLES

The following descriptions of various examples are not intended to limit the scope of the claims to the precise form or forms detailed herein. Instead the following descriptions are intended to be illustrative so that others may follow their teachings.

Example 1

Signal Propagation

Figure 2:
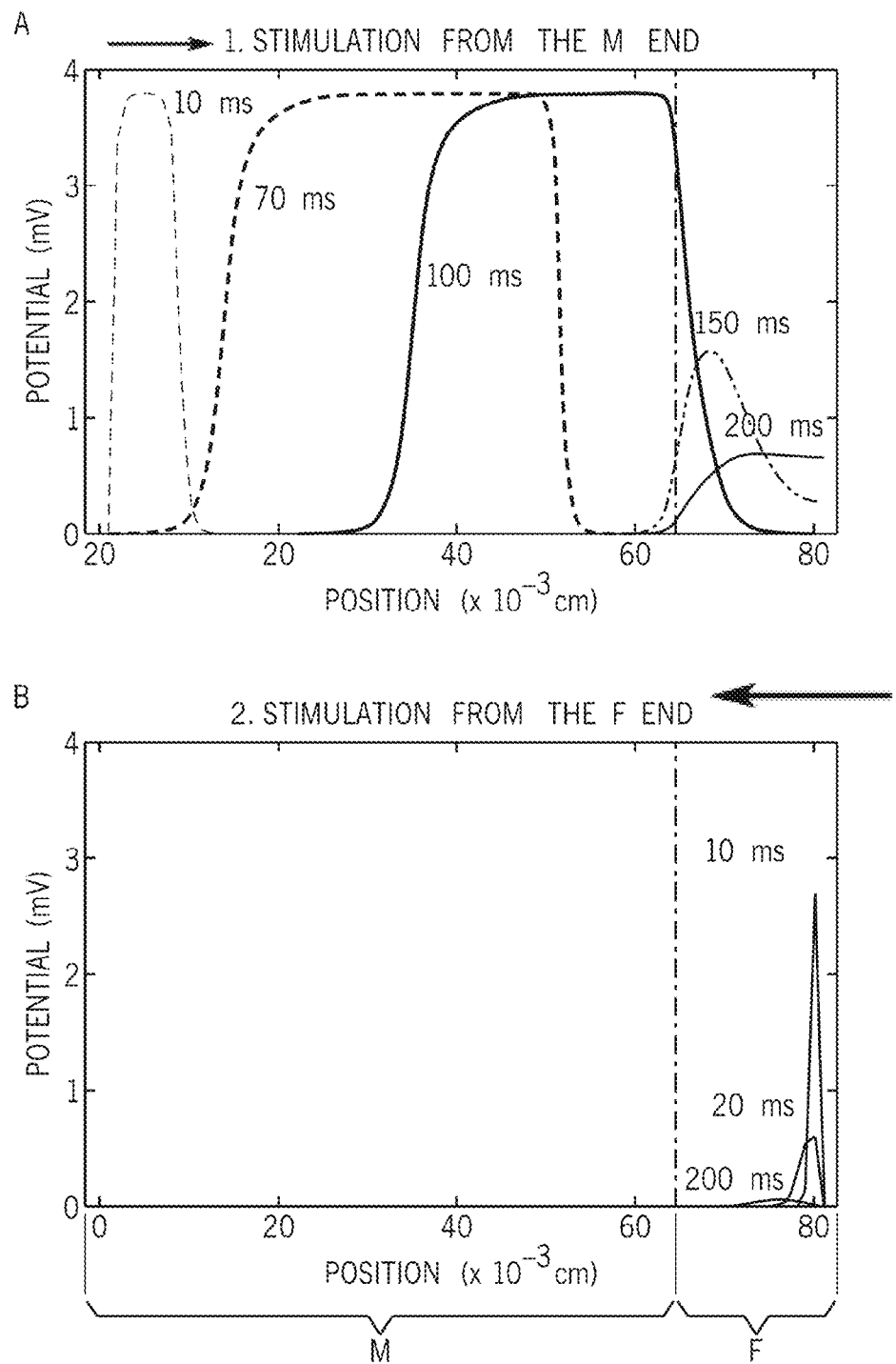
FIG. 2. Data on signal propagation. Computer simulation of electrical stimulus (3 mV, for 0.1 ms.) propagation within a micropatterned excitable (red lines, muscle cell (M))/non-excitable (black lines, fibroblasts (F)) cell co-culture in forward (from the muscle cell end) (A) and in reverse (from the fibroblast cell end) (B) directions (the dashed vertical line marks the excitable/non-excitable cell border).

FIG. 2 shows the response of an 800 μm long cardiac muscle cell-fibroblast chain. First, a pulse was initiated by stimulating a single heart muscle cell for 0.1 ms by 3 mV. The electrochemical wave propagates through the cardiac cells without loss until it reaches the fibroblast boundary at x=640 μm, shown by the vertical line (FIG. 2A). As expected, upon reaching the fibroblast region the electrochemical wave rapidly attenuates. One can evidently tune the length of the fibroblast chain to achieve a desired signal output level. When the other end of the chain is stimulated by the same signal, the signal rapidly attenuates (FIG. 2B). By the time the signal reaches the muscle-fibroblast boundary it is orders of magnitude below the muscle excitation threshold, and therefore cannot pass through.

Example 2

Cell Micropatterning

Figure 3:
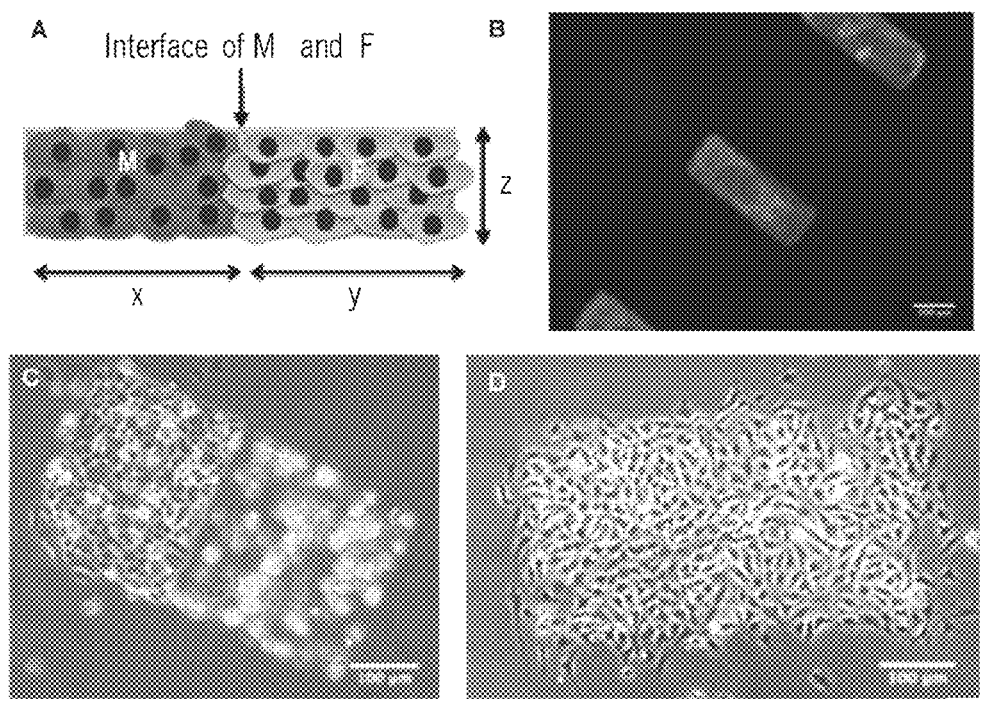
FIG. 3. Data on Cell Micropatterning. A) Schematic representation of excitable (muscle—M) and non-excitable (fibroblast—F) cell distribution on micropatterned surfaces. Two parameters (1) excitable to non-excitable cell ratio (x/y) and (2) the amount of interfacing excitable and non-excitable cells (z) will be varied in order to achieve directional signal transduction. B) Microcontact printed Alexa 488 conjugated-fibronectin on glass substrates showing multiple patterns (green). Higher magnification images of fibroblast (C) and cardiac muscle cell (D) seeded micropatterns. C) Microfabrication techniques used to pattern 2 cell types on the same cell pattern in a controlled manner (overlay image of bright-field and cell tracker stained cells (blue)—the second cell type is tracked by blue cell tracker dye), and D) only cardiac muscle cells seeded confluently on a micropattern (overlay of bright field image showing the cells and fluorescence image showing the protein pattern (green)).

Stamps were fabricated and used for micropatterning Alexa 488-conjugated fibronectin in order to examine patterning fidelity (FIG. 3B). Micropatterned cell adhesive protein was seeded with fibroblasts (FIG. 3C) and cardiomyocytes (FIG. 3D and FIG. 4A) and imaged using bright field and fluorescence microscopy. 2-cell patterning approach using cell tracker stained cells have tested.

FIG. 3C shows an overlay image of fluorescence and bright field images of the same pattern. The second cell seeding was performed using Blue CellTracker stained fibroblast cells, while the first seeding was performed by unstained cells, showing more than 95% effective localization of the distinct cell types as patterned.

Neonatal rat ventricular heart cells isolated from 2-day-old Sprague-Dawley rats were used as a model cell source following a well-established protocol. The cardiac muscle cells and the fibroblasts were separated through 2 hour pre-plating in Dulbecco's modified eagle medium supplemented with 10% fetal bovine serum and antibiotics under normal cell culture conditions. Briefly, all the isolated cells were placed on tissue culture plates. As muscle cells require longer time to attach to tissue culture substrate, the first cells to be attached are fibroblasts. Other cells present in the heart wall tissue (i.e. endothelial cells) were mostly eliminated due to the specific media used. Fibroblasts attach to the flask surface during this pre-plating, and will continue to be cultured until they were seeded on the patterned surfaces. Fibroblasts were subcultured for several passages to ensure their enrichment. As the cardiac muscle cells are non-dividing cells, any remaining cardiac muscle cells were eliminated during this sub-culture period. For all experiments, fibroblasts with passage numbers 4 to 8 were used. The unattached cells at the end of the 2 h period were heart muscle cells. The double cell seeding were performed as proven successfully (FIG. 3C). Briefly, cardiac muscle cells were directly seeded on the micropatterned substrates immediately after their isolation, and incubated for 24 h for the cells to attach. The substrates were then washed once with culture media to remove any unattached cells, and the stencil was removed. The fibroblast cells were seeded on the micropatterned substrates, and after waiting for 50 min for the fibroblasts to adhere to the open spots on the micropatterned substrates, the substrates were washed once more, and cultured up to 5 days using the same media under normal cell culture conditions.

Example 3

Figure 4:
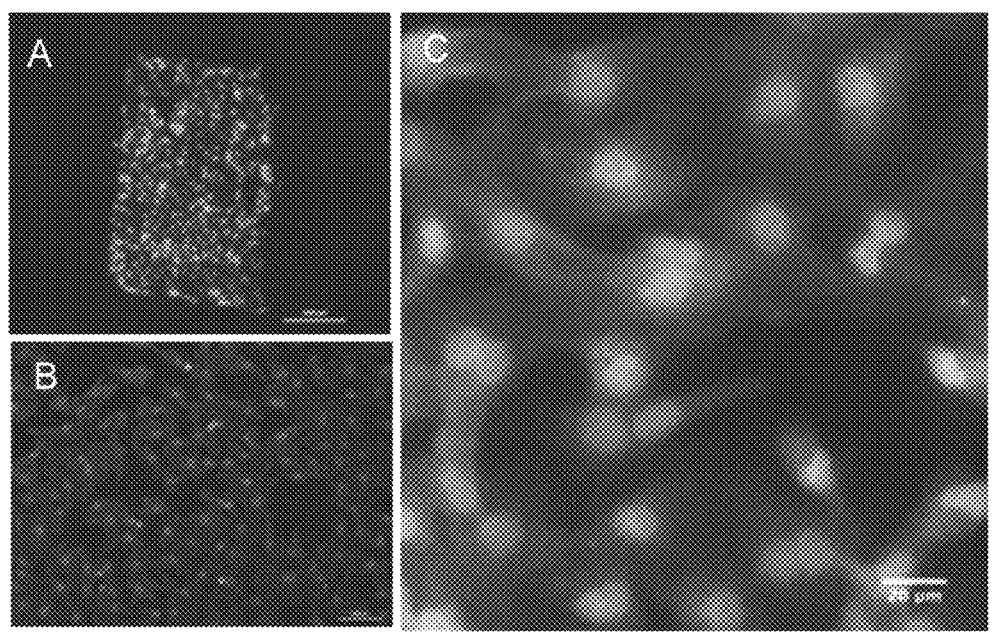
FIG. 4. Data on isolation and culturing of excitable cardiac muscle cells and non-excitable cardiac fibroblast. Cells were double immunostained for Vimentin (red) and Cardiac Troponin I (green). A) Isolated cardiomyocytes seeded on micropatterns, B) Isolated and sub-passaged cardiac fibroblasts (passage 4), C) High magnification image if cardiac muscle cells showing striations.

Isolation and Culturing of Excitable Cardiac Muscle Cells and Non-Excitable Cardiac Fibroblasts FIG. 4 shows Vimentin (fibroblast marker) and Cardiac Troponin I (cardiomyocyte marker) staining of the isolated cardiomyocytes (FIGS. 4A and C) and fibroblasts (FIG. 4B). These studies showed that striated cardiomyocytes have been cultured using the methods disclosed herein, indicating the presence of healthy cardiomyocytes. And while there are a few fibroblasts observed among the micropatterned cardiomyocytes (red cells in FIG. 4A), there were no cardiomyocytes in the fibroblast culture (FIG. 5B).

Example 4

Characterization of the Micropatterned Cells

Cell viability, spontaneous apoptosis, metabolic activity and the expression of functional proteins and phenotypic markers are analyzed on days 1, 3, and 5 after the cell seeding. Cell viability is assessed over time using a live-dead calcein AMethidium homodimer viability assay. Apoptosis is quantified using a colorimetric TUNEL assay and a colorimetric caspase 3 assay. The metabolic activity is examined performing a mitochondrial activity assay such as AlamarBlue. To determine the contractile muscle cell phenotype, protein markers sarcomeric α-actinin (SαA) and troponin-I are examined by immunostaining. Fibroblast phenotype are determined by immunostaining for discoidin domain receptor-2 (DDR-2). The cell-cell junctions between these cells are also be examined immunostaining for connexins and cadherins. Specifically, Connexin-40, Connexin-43, Connexin-45 and N-cadherin presence and localization among the two cell types, and in the interface between the two cell types are quantified. The fibroblast and muscle cell localization, and cell-cell junction formation are examined by triple immunostaining for DDR-2 (fibroblasts), troponin-I (heart muscle cells) and either Connexins (gap junctions) or cadherins (adherens junctions). Degree of gap junction and adherens formation is quantified using high magnification fluorescence images and NIH ImageJ image analysis software. The spontaneous beating behavior and synchronization of the muscle cells are analyzed through microscopy recordings every day starting with day 2. The recordings are analyzed using a custom-made MATLAB code and quantified up to 10 days.

Example 5

Electrical Response

Figure 5:
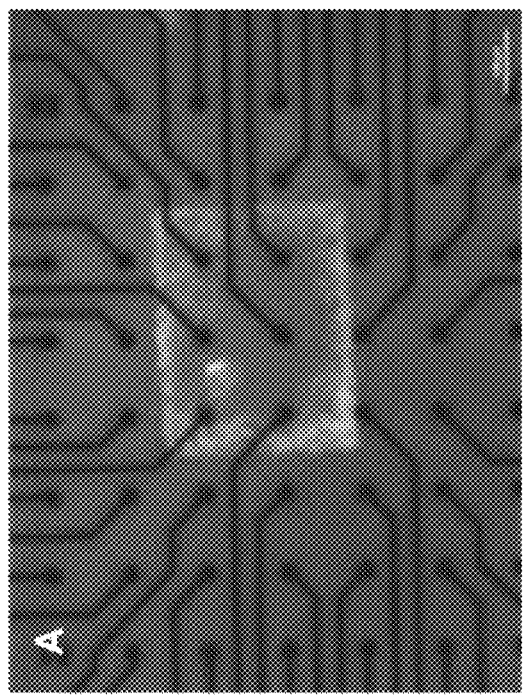
FIG. 5. Data on analysis of electrical signal propagation. A) Fibronectin micropatterns on Microelectrode Arrays and B) cardiomyocytes seeded on the array, confined to the micropatterns (right) (scale bar: 100 μm).
Figure 5:
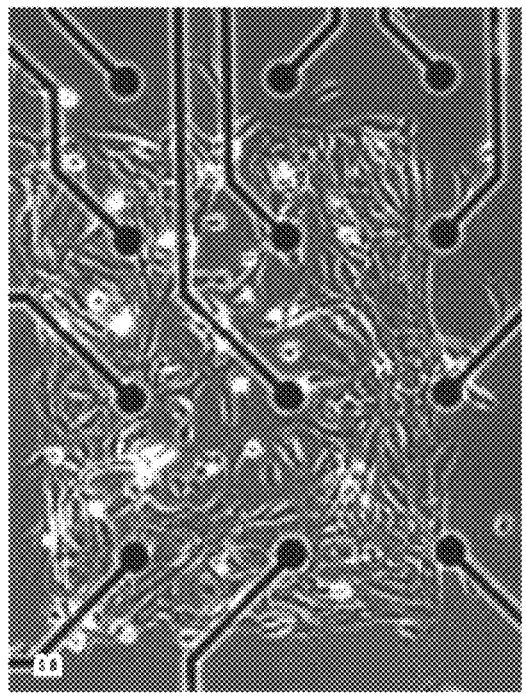

The electrical response of the micropatterned cells was examined using a state-of-the-art microelectrode array system (ALA Scientific Instruments, MEA2100-60). This system allows simultaneous stimulation and recording of electrical signals up to 60 channels, with the capability of assigning recording and stimulation functions to individual channels. Since the microelectrode array substrate is transparent, simultaneous imaging of the ion influx between adjacent cells is also possible. The cells were micropatterned on the substrates with embedded electrodes (FIG. 5). Membrane voltages of the cells confined in the micropatterns were recorded while stimulating the patterned cells from various different locations within the pattern. Cells were pre-loaded with Fluo 4 AM Calcium sensitive dye for concurrent calcium flux analysis. Prior to coupling this system with the AFM/3d optics for absolutely unique measurements in the world, the electrical stimulation responses were implemented on a separate spinning disk confocal system with a highspeed camera (Hamamatsu Orca13). To investigate the diode function of the micropatterned co-cultures, currents with amplitudes ranging between 200 to 400 $\mu A/cm^2$ were applied to microelectrodes positioned at one edge or another of co-cultured patterns, allowing membrane voltage changes, and the intercellular ion flux, to be recorded for both forward and reverse directions.

Example 6

Mechanical Response

Figure 6:
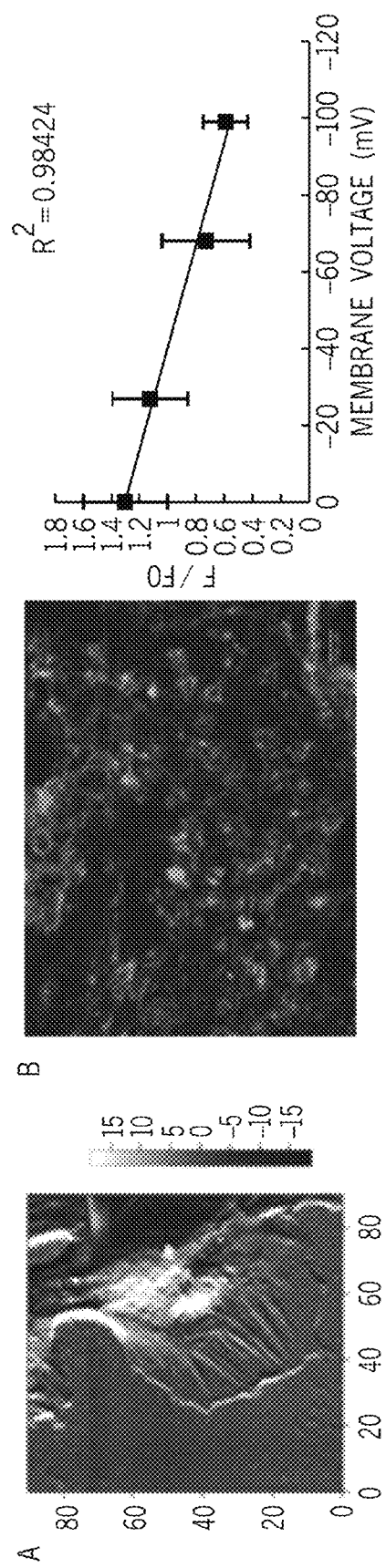
FIG. 6. Data on AFM characterization and mechanical signal propagation. A) AFM surface scan of a single cardiomyocyte in the micropatterned cell patch showing a healthy cardiac muscle cell morphology. B) Voltage sensitive dye staining of cardiomyocytes (left) and the calibration curve corresponding to membrane hyperpolarization (right) C) Mechanical stimulation using a colloidal probe from one end of the micropatterned cardiomyocyte patch (left). The frequency of the synchronously beating patch was altered upon mechanical stimulation (i.e. single cell poking at 5 Hz) and cell patch assumed the beating rate of the poke as measured using intensity analysis of the simultaneously recorded bright filed video (right).
Figure 6:
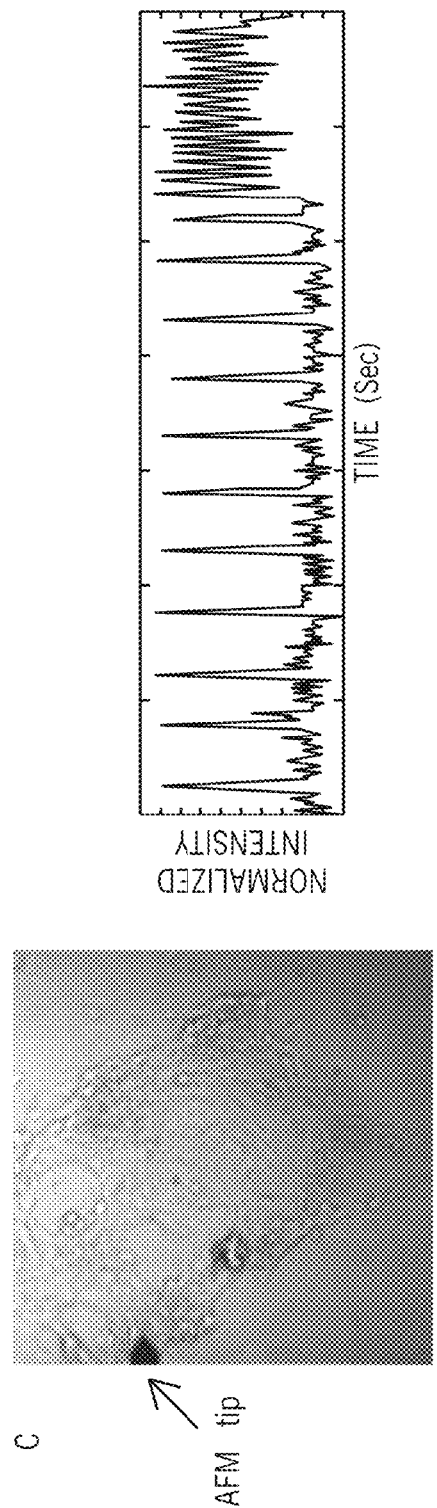

Mechanical stimulation and signal transduction studies were carried out in the AFM/3d optics system already introduced. Typically, silicon nitride cantilevers with 0.06 N/m spring constants were employed, allowing high resolution cell images (FIG. 6A) with fine force control and resolution (pN to few nN). Again, single cells from either end of the diode pattern were mechanically stimulated under contact mode (i.e. poking), typically with commercially available spherical AFM probes (5 um radius) to minimize the local pressures applied during such nanoscale loading. Simultaneous calibrated ion flux imaging (FIG. 6B), and eventually also MEA-based membrane potential mapping, could therefore monitor the mechanical, chemical, and electrical signal distribution for forward and reverse diode functions.

AFM controlled cell beating was demonstrated (FIG. 6C), in which an AFM probe was positioned at the edge of a patch of micropatterned cardiomyocytes and initially simply contacts a cell to monitor the regular, several micrometer cell membrane expansion and corresponding ~10-100 nN forces. Prior to mechanical stimulation, micropatterned cell patch was beating synchronously with a typical period of ~5 sec, identified by analyzing simultaneously acquired video of the fluorescent markers, apparent cell volume, or in this case the intensity change upon cell motion (as graphed). When the AFM begins indenting a single cell at a rate of 5 Hz, approximately 50 sec. into the experiment, the patch synchronizes with the mechanical signal, essentially achieving 'nano-cpr.'

Simultaneous indentation data during the AFM 'compressions' are provided a continuous measure of the cell stiffness as well. A reversible actin cytoskeleton interrupting molecule, such as butyl benzyl phthalate (BBP), is also be used to examine the mechanism for transduction of the AFM-induced input signal. This allows distinguishing between a mechano-transduction that happens through the cell-cell adherens junctions that can relay through the cell cytoskeleton, and mechano-electric feedback that results from electrical excitation of mechanically stimulated cardiac cells. To further the development of cell-based diodes, the AFM is positioned to detect forces at any location within electrically stimulated cell diodes as well, allowing mapping of the mechanical propagation between or within single cells.

Example 7

Studying the Response of Myocardial Cells to Electrical Stimulation

Figure 8:
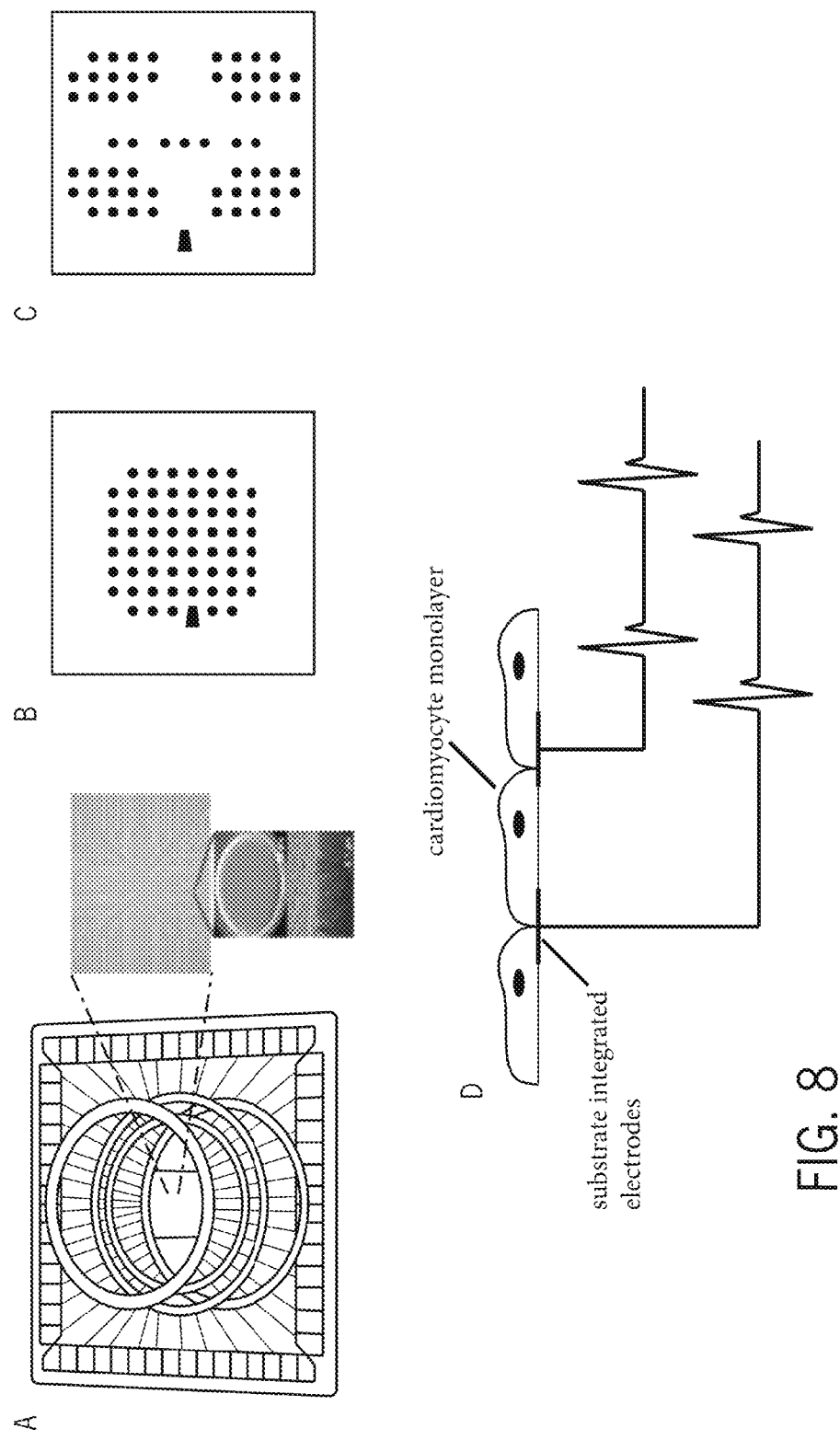
FIG. 8. MEA substrates (a); Electrode layout for PEDOT MEA array (b) and for 4Q MEA array (c); schematics of the electrical signal recordings from cells cultured on these substrates (d).

In order to study the electrical signal propagation within micropatterned co-cultured myocardial cells and to test their diode-like properties we used a state-of-the-art Microelectrode Array (MEA) system (Multichannel Systems GmbH, Germany). The substrate that the cells were cultured on consists of a glass base with embedded electrodes made of Titanium Nitride (TiN) or Gold (Au), surrounded by Au recording pads and a reference electrode (FIG. 8). Simultaneous recording and stimulation of cells can be carried out using these electrodes and the signals are transmitted to the MEA system through the Au recording pads (FIG. 8a). The MEA distribution on the substrates can be arranged as needed. In this study we used two types of MEA substrates with different microelectrode distributions: 1) 60Pedot-MEA200/30iR-Au (PEDOT MEA), with an 8×8 carbon nanotube (CNT) electrode grid, each electrode with 30 µm diameter and with 200 µm inter-electrode spacing (FIG. 8b) and 2) 60-4QMEA1000iR-Ti (4Q MEA) with TiN electrodes, 30 µm diameter electrode size with 4 microelectrode grids of 13 electrodes each and a center line with 7 electrodes (FIG. 8c). Myocardial cells were cultured as micropatterned monolayers on the surface of the microelectrodes (FIG. 8d).

The measurements were performed in culture media using a temperature-controlled chamber. All measurements and pacing were performed on day 4 of the CM seeding, and within an hour of placing the samples in the MEA system. Spontaneously beating cultures were beating at a rate of 0.5 to 1.5 Hz prior to measurements and stimulation. In some of the experiments, cells that are not initially beating were electrically stimulated to start beating. Stimulations parameters used throughout the experiments were 400 mV with 1 Hz or 2 Hz frequency and 30 repeats. Data acquisition and setup of the stimulation electrodes were performed using the MEA system's software MC Rack. Frequency of the signals was analyzed using MATLAB.

Example 8

Figure 9:
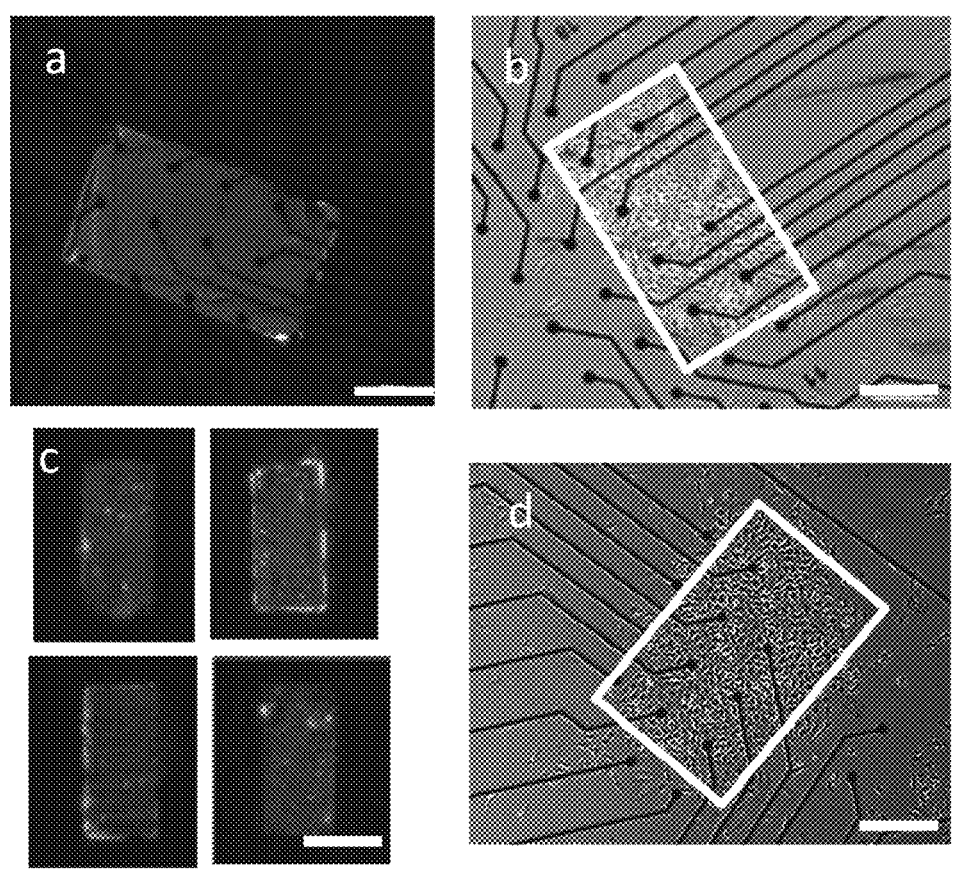
FIG. 9. Fibronectin pattern (left) and confluent attachment of CMs (right) on PEDOT MEA (a, b) and on 4Q-MEA (c,d) (Scale bar: 200 μm).

Membrane Potential Measurements and Electrical Stimulation of CMs Using the MEA System To obtain controlled population of CM, extracellular matrix (ECM) protein fibronectin was microcontact printed as rectangular patterns (450×900 µm), on the MEA substrates following the micropatterning procedures optimized in the previous section (FIG. 9). For patterning on the MEAs, PDMS stamps with micropattern dimensions that match the layout of the electrodes on the MEA substrates were designed and fabricated (FIG. 9).

After patterning the CMs on the MEA substrates, the membrane potentials of these cells were recorded using the MEA system. Following the recording of their baseline spontaneous electrical activity, the CMs were also electrically stimulated using the MEA system and the beating frequency change in response to the electrical stimulation (FIG. 9) as well as the electrical signal propagation between the subsequent electrodes (FIG. 9) were recorded.

The membrane potential of the spontaneously beating CMs was recorded at 1 to 3 mV (±0.5 mV to ±1.5 mV) (FIGS. 10 and 11), which is typical for neonate membrane potentials recorded using surface electrodes. Note that since we perform the recording from the surface of the cells only, as oppose to recording the potential change between the two sides of the membrane, the recorded values are much smaller than classic electrophysiology experiments using patch-clamp.

Figure 10:
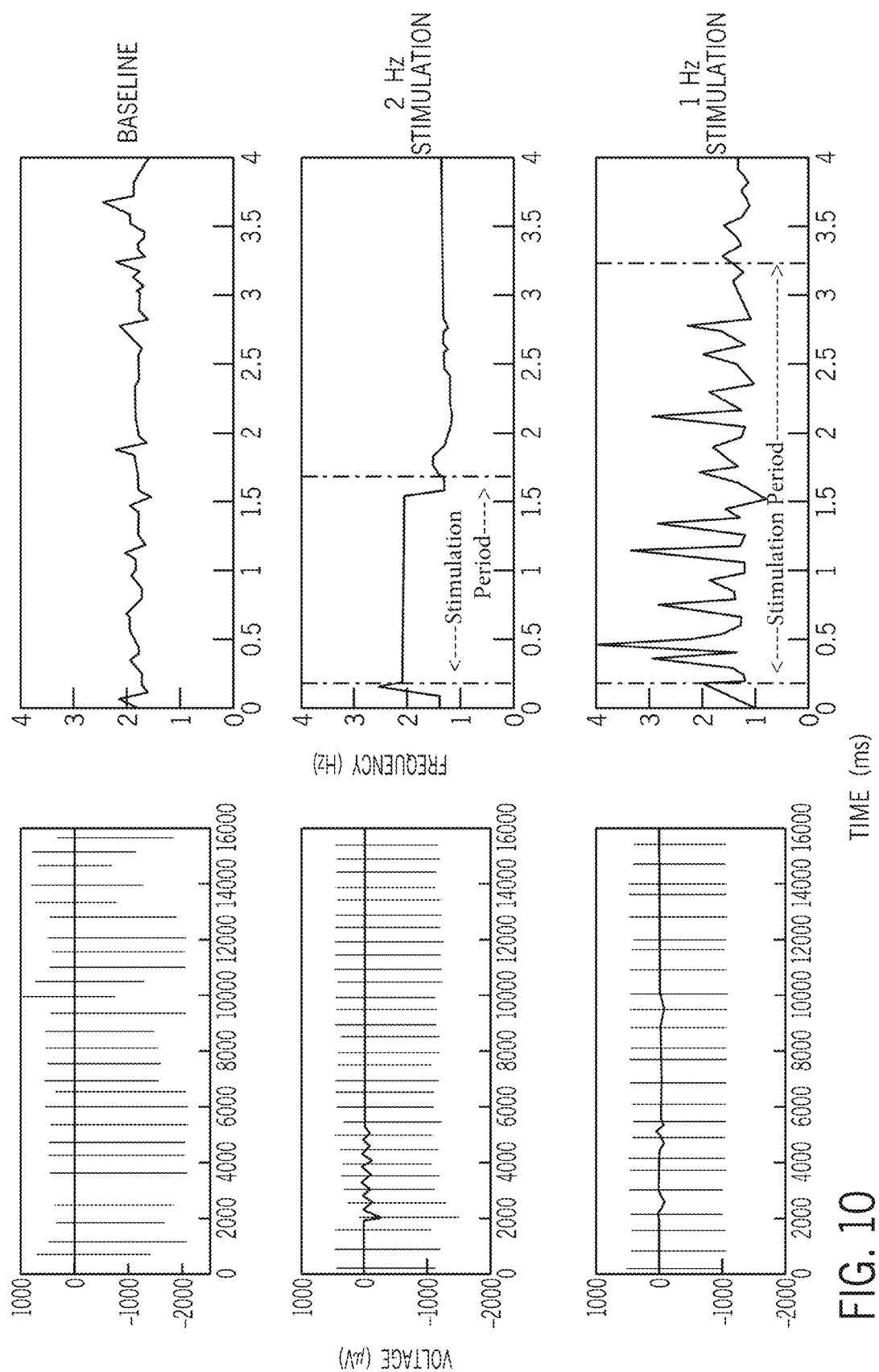
FIG. 10. Baseline recording, 2 Hz and 1 Hz stimulation of the CMs using the MEA system.
Figure 11:
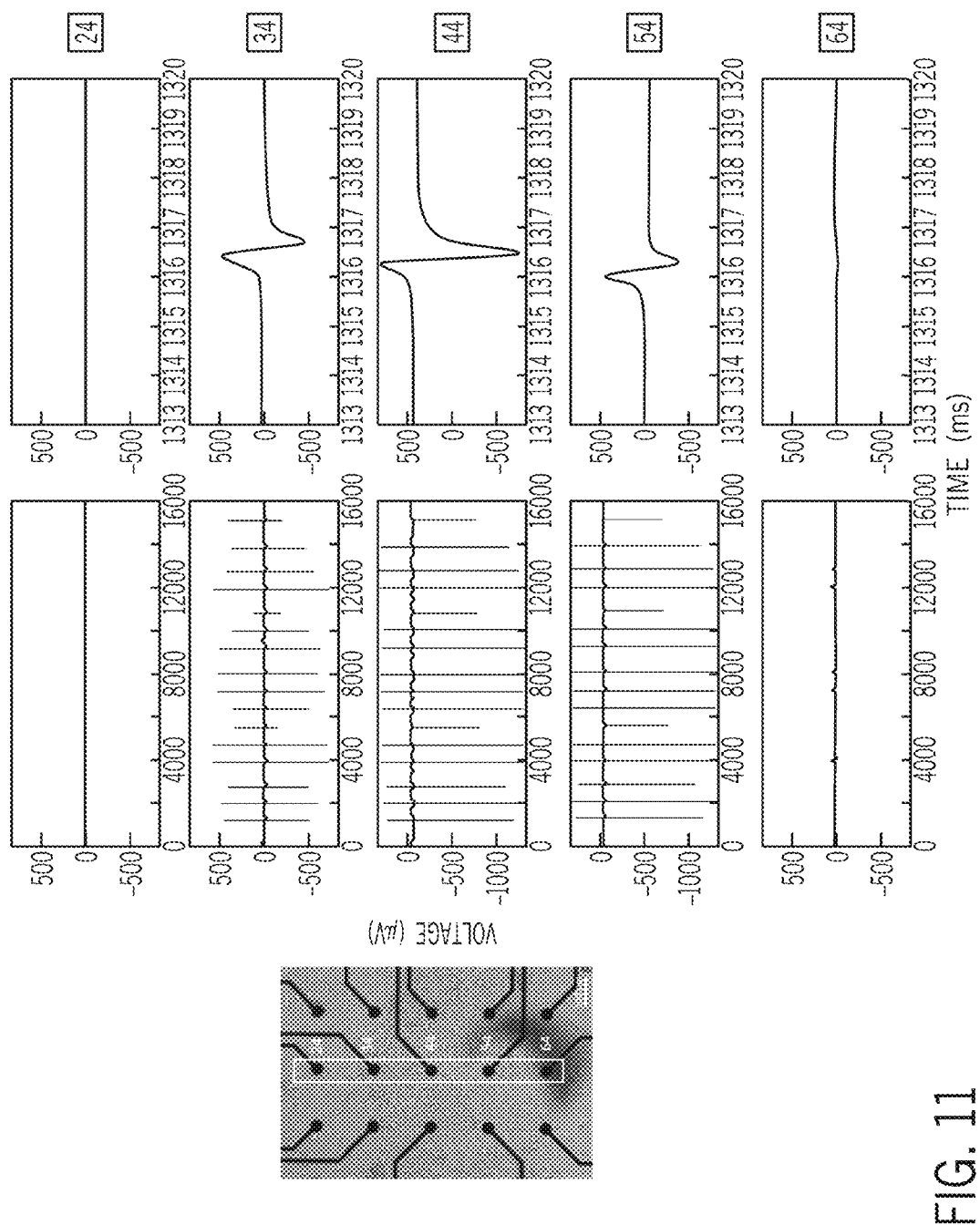
FIG. 11. Spontaneous electrical activity of the micropatterned CMs (right) and corresponding bright field image (left). There were no CMs on electrodes 24 and 64 and the CM micropattern was constrained between electrodes 34-54.

When the CMs were stimulated at higher frequencies than their spontaneous beating rate, they were paced to beat at the stimulation frequency. However when stimulated at lower frequencies than their spontaneous beating frequency, the cells did not slow down to pace with the stimulation frequency (FIG. 10). FIG. 10 shows results of an experiment where the spontaneous beating frequency of CMs (baseline recording) was slightly less than 2 Hz. CMs' beating frequency paced at 2 Hz upon 2 Hz stimulation, while 1 Hz stimulation did not cause the CMs to slow down to 1 Hz beating rate. We also measured the electrical signal propagation between the subsequent electrodes during the spontaneous beating of the CMs and ensured that there were no signals recorded from electrodes without any CMs (i.e. electrodes 24 and 64) (FIG. 11).

Example 9

Figure 12:
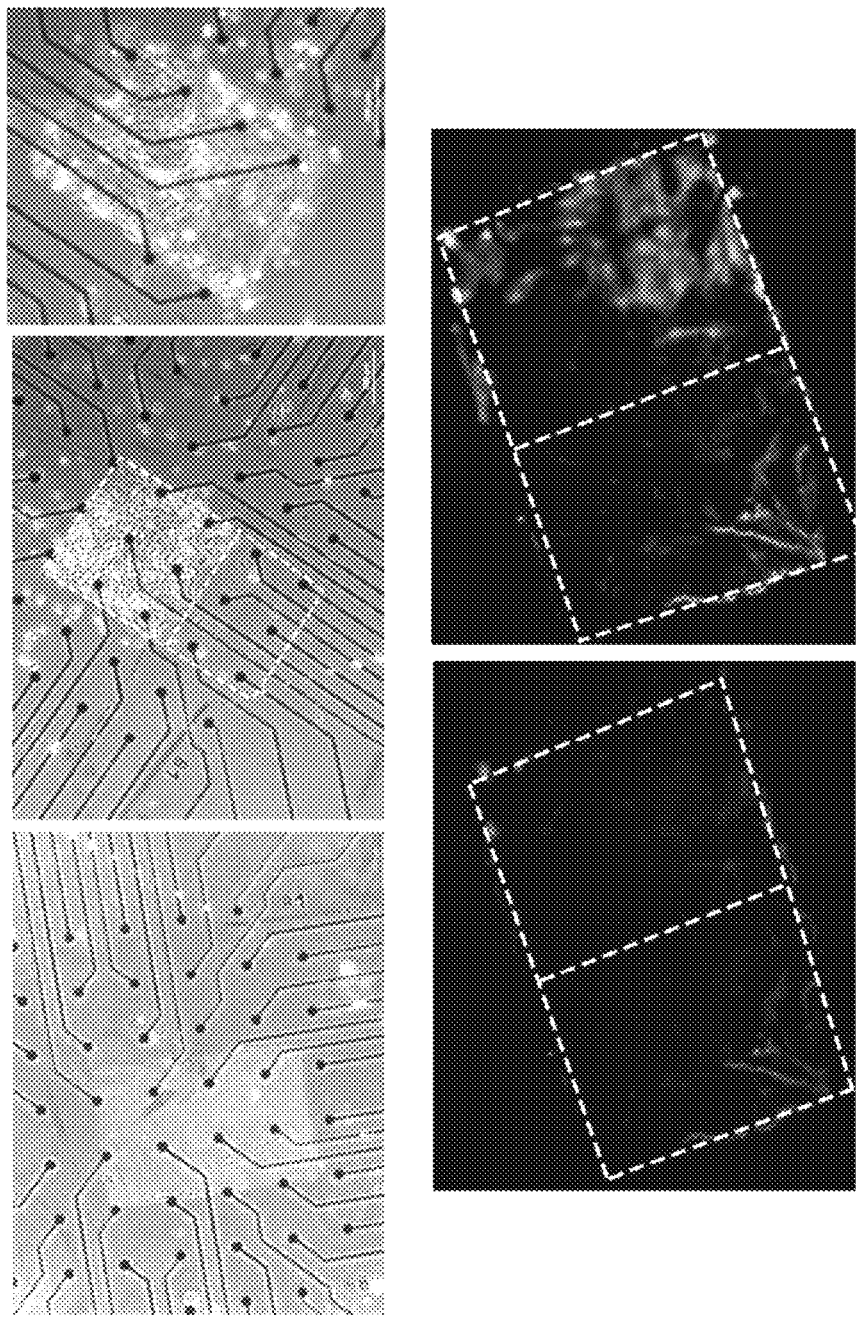
FIG. 12. Top panel from left to right—fibronectin pattern, cells after first seeding (CMs) and after second seeding (CM-CF co-culture) (a); Bottom panel—Calcium flux imaging (2 subsequent images from the acquired movie) of the co-cultured CMs on the MEA substrates showing synchronous beating of the CMs (b) (Scale bar: 200 μm).

Membrane Potential Measurements and Electrical Stimulation of Cardiomyocyte-Cardiac Fibroblast Co-Culture Using the MEA System To obtain micropatterned co-cultures of CMs and Cardiac Fibroblasts (CFs) on the MEA substrates, thin film stencils made of parafilm and PDMS were used to partially block the rectangular microcontact printed fibronectin patterns (450× 900 μm). We followed the same micropatterning procedure we developed for creating CM-CF co-cultures on the glass coverslips for creating CMCF co-cultures on the MEA substrates. Briefly, the rectangular fibronectin pattern was partially covered with thin PDMS or parafilm stencils, the first cell type (CMs) was seeded and cultured for 2 days, allowing the CMs to attach and spread (FIG. 12). After 2 days, the stencil is removed and the second cell type (CFs) was seeded on the initially covered half of the pattern. FIG. 12a shows the patterned co-culture, the CMs were stained with red cell tracker and the CFs were stained with blue cell tracker. The patterned co-cultures on the MEA substrates were also examined for their Calcium flux using Calcium Fluo 4 dye as described in Section 1 to confirm cell viability, function and synchronous beating activity (FIG. 12b).

Figure 13:
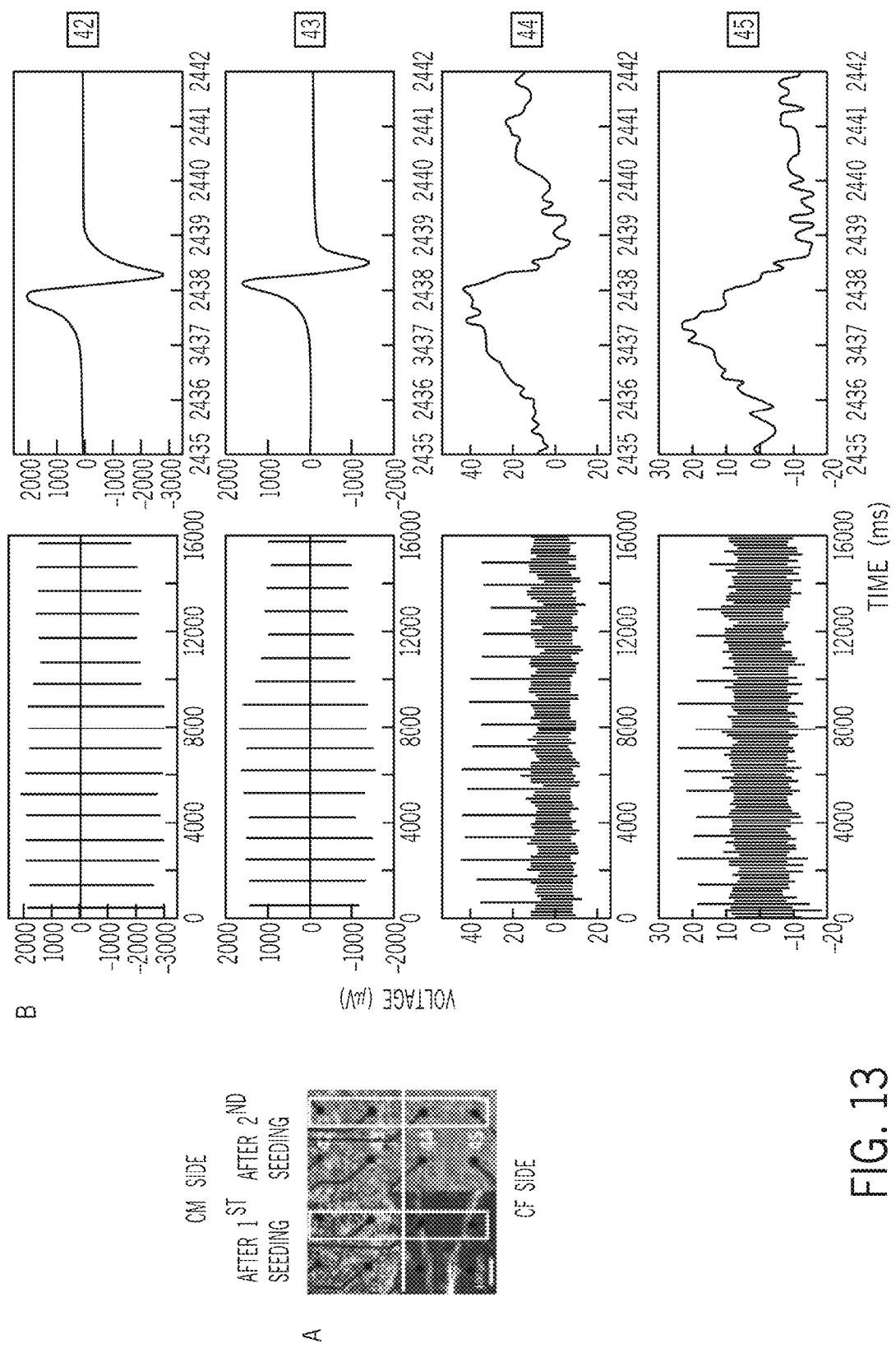
FIG. 13. Membrane potential recordings of the spontaneous electrical signal propagation in micropatterned CM-CF co-culture. A) Bright field images of the CMs and CFs in co-culture on MEA substrate, showing only CMs following the first cell seeding (left) and showing both the CMs and the CFs after the second seeding (right). CMs are located on electrodes 42 and 43 and CFs are on electrodes 44 and 45. B) Corresponding membrane potential recordings showing the long-term (column on the left) and short-term (column on the right, zoom in to one of the spikes in the long-term scale) time frames.

Next, we recorded the electrical signal propagation between the micropatterned CM and CF cocultures. FIG. 13 shows the results of recording of membrane potentials of the co-cultured cells where CMs were spontaneously beating without any stimulation. The spontaneous membrane potential fluctuation of the CMs was recorded to be at around ±1.5 mV. Attenuation of this signal as it propagated from CMs through the CFs along electrodes 42 to 45 was recorded (FIG. 13). Although its amplitude is much smaller compared to the CM signal (electrodes 42 and 43), which was around ±40 μV compared to ±1.5 mV of the CMs, the membrane potential fluctuations caused by the incoming CM signal can clearly be seen in the CF channels (electrodes 44 and 45).

Figure 14:
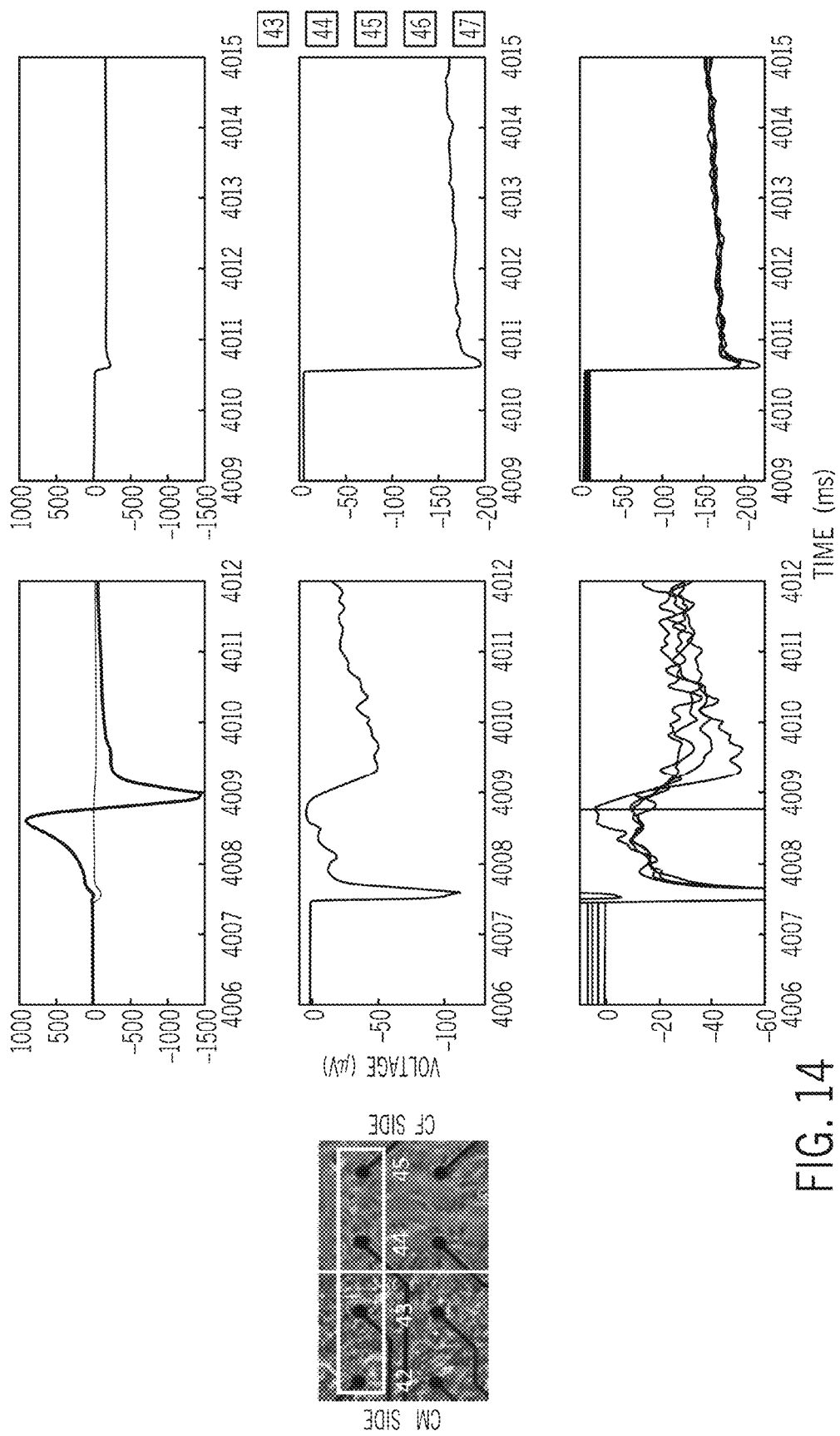
FIG. 14. Membrane potential recordings from CMs (43) and CFs (44-47) upon stimulation from CMs side (from electrode no. 41) (left) and stimulation from CFs side (from electrode no. 47) (right).

The diode-like behavior of CM-CF co-culture was studied through membrane potential recordings upon electrical stimulation. In order to achieve this, following the membrane potential measurements of spontaneously beating cells, the co-culture was stimulated from the CM and CF sides sequentially (FIG. 14). Similar to spontaneously beating CM-CF co-culture, signal propagation and attenuation in the CF electrodes was observed upon stimulation from the CM side. On the other hand stimulation from the CF side did not initiate any response on the CMs, as expected. The only electrical fluctuation recorded in these channels was the stimulation artifact (the sudden drop in the potential that can be seen in all channels just before the biological signal recorded from the cells).

The response of the CMs to the stimulation can clearly seen in electrode no. 43 (blue line) when the stimulation signal was sent from the CM side, while no response was observed when stimulation signal was sent from the CF side (top row in FIG. 14). The stimulation signal from the CM side propagated to the CF side and was detectable on the CF electrodes (no. 44) (orange line, middle row in the FIG. 14). The signal attenuated as it propagated further away from the CMs (bottom row in FIG. 14).

Example 10

Fabrication of PDMS Stencils and Sheets

In order to create micropatterned surfaces, SU-8 2075 (MicroChem Corp.) photoresist was spin coated (1000 rpm, 300 rpm/s, 30 s) to obtain a thickness of 200±20 μm on a silicon (Si) wafer (University Wafer), following manufacturer's instructions. PDMS (Ellsworth Adhesives) base and curing agent were mixed in 5:1 ratio, degassed, spin coated on the silicon wafers (750 rpm, 100 rpm/s, 30 s) and cured at 70° C. for 30 minutes.

Example 11

Cell Isolation and Culture

Micropatterned substrates were seeded with neonatal rat ventricular cardiac cells isolated according to a previously established protocol[33] and following regulations of University of Notre Dame's Institutional Animal Care and Use Committee. The culture was maintained under standard cell culture conditions in Dulbecco's Modified Eagle Medium (DMEM, Hyclone) supplemented with fetal bovine serum (FBS, 10%, Hyclone) and penicillin-streptomycin (P/S, 1%, Corning). Endogenous fibronectin was removed from the FBS using gelatin sepharose 4B (GE Healthcare).

Fabrication of the MCD: Fibronectin (50 μg/mL, Sigma-Aldrich)/Alexa-488 or Alexa-647 tagged fibrinogen (50 μg/mL, Molecular Probes) solution was added on top of the stencil and was incubated at 37° C. for 30 minutes. Following a phosphate buffered saline (PBS, Corning) wash, stencils were removed. Then MEA surfaces were coated with Pluronic F127 (1% solution in water, Sigma-Aldrich), for 1 hour. CM cell enriched, CF containing cell suspension was seeded at a density of 0.5×106 cells/ml and incubated overnight and the PDMS sheet was peeled off. In 4-5 days the CF cells proliferated to fill the pattern.

Example 12

Ca2+ Indicator Loading

Co-culture was loaded with Fluo-4 acetoxymethy ester (Molecular Probes), which exhibits increase in fluorescence intensity upon binding to Ca2+, following manufacturer's instructions.

Example 13

Electrical Signal Measurements and Stimulations

Electrical field potential measurements were performed using the MEA-2100 system (Multichannel Systems) with a sampling rate of 2.5 kHz. Cells were stimulated with ±400 mV, 1 ms biphasic pulses of various frequencies (i.e., 1 Hz, 2 Hz, 3 Hz). Biphasic pulses were achieved by using two electrodes simultaneously for stimulations.

Example 14

Data Acquisition and Plotting

Data sets from electrical measurements were exported and plotted using MATLAB. All data sets (spontaneous activity and response to stimulations) were collected from both the CM cell and CF sides of the culture simultaneously. For the spontaneous activity measurements, each individual AP was detected by a 40 μV threshold from the CM cell side. For the stimulation measurements, the signals collected were plotted using the stimulation instant (precisely defined by the input signal) as t=1 μs for each individual stimulation. For all cases these signals were plotted using raw data (gray curves) and then averaged (red and green curves). The distance between two electrodes of the MEA was divided by the time the AP required to propagate from one electrode to another in conduction velocity calculations. This time difference was calculated by comparing the times measured from these two electrodes when the maximum voltage occurs.

Example 15

Cell-Based Diodes

Figure 15:
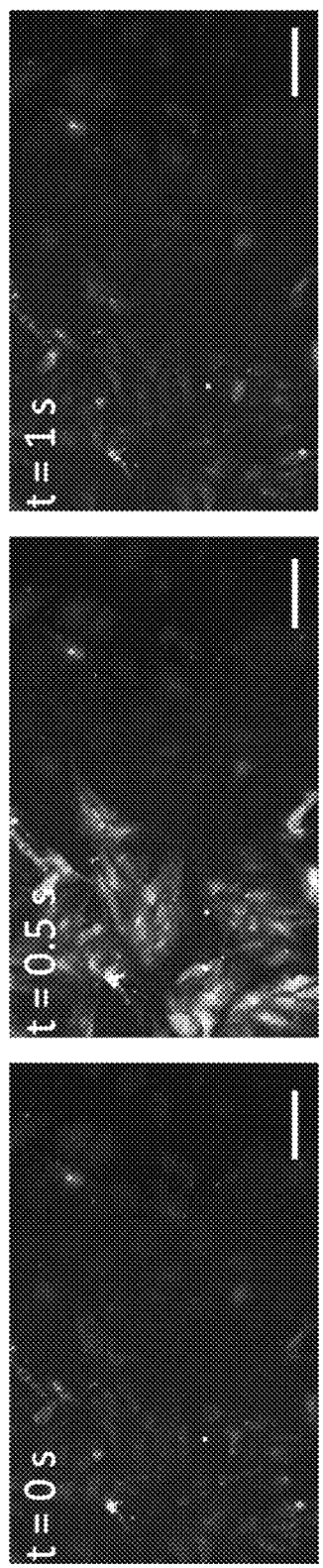
FIG. 15. $Ca^{2+}$ flux (green) imaging of the micropatterned cardiac muscle cell (CM, left) and cardiac fibroblast (CF, right) co-culture (a, scale bars: 100 μm, see Supplementary Movie 1 for the video file). Baseline activity (b, top), stimulations from excitable CM (b, middle) and non-excitable CF (b, bottom) sides of the co-culture. For all three cases, individual, consecutive AP events (gray) were drawn and averaged (green for CM cells or red for CFs).
Figure 15:
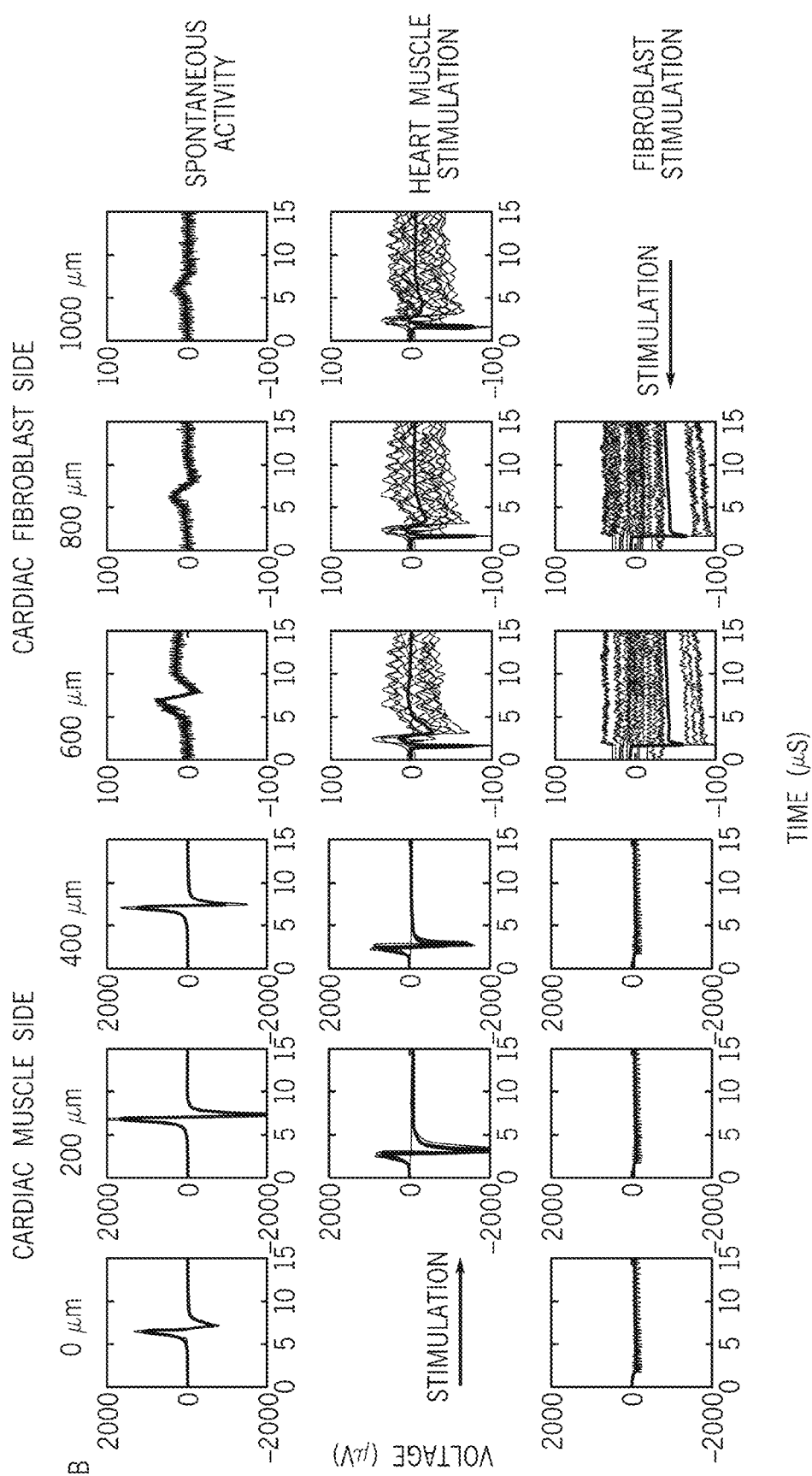

Diode-like nature of the heart muscle cell and the fibroblast co-culture was shown by both spontaneous electrical activity measurements and stimulations of a micropatterned co-culture of these two cell types (FIG. 15). In these experiments where we assessed the diode like nature of a directional excitable-non-excitable cell connection, we created regions with excitable cells and non-excitable cells by partially blocking the MEA substrate surface with a thin PDMS sheet.

$Ca^{2+}$ ions activate myofilaments and cause contractions in cardiomyocytes. In order to visualize $Ca^{2+}$ transportation during contraction-relaxation periods and to confirm the functionality of the micropatterned cells we captured $Ca^{2+}$ flux by time-lapse fluorescence microscopy during their spontaneous beating (FIG. 15a). This result also confirmed the spatial localization of excitable and non-excitable cells within the culture.

Next, we measured the extracellular membrane potentials from both the excitable and the non-excitable cells using microelectrodes (MEAs) (FIG. 15b). MEAs in this study consist of poly-3,4-ethylenedioxythiophene-carbon nanotube (PEDOT-CNT) electrodes with electrode spacing of 200 μm and electrode diameter of 30 μm. Electrical field potential measurements from these electrodes were performed using to MEA-2100 system (Multichannel Systems) with a sampling rate of 2.5 kHz. Briefly, the MEAs were placed onto the head stage to read or write the electrical signals through the contact pads of the MEAs. The signals read by head stage pins were transferred to a PC using the interface board. Using a temperature controller unit (TC02, Multichannel Systems) temperature was kept constant at 37° C. throughout the experiments. Cells were stimulated with ±400 mV, 1 ms biphasic pulses of various frequencies (1 Hz, 2 Hz, 3 Hz). MEAs used in this study allow simultaneous stimulation and recording of electrical signals up to 60 channels, with the capability of assigning recording or stimulation functions to individual channels. Biphasic pulses were achieved by using two electrodes simultaneously for stimulations.

Data sets from electrical measurements were exported and plotted using MATLAB. All data sets (spontaneous activity and response to stimulations) were collected from both heart muscle and fibroblast side of the culture simultaneously. For all cases, these signals were plotted using raw data (FIG. 15b, gray curves) and then averaged (FIG. 15b, red and green curves). While gray curves represent individual AP events occurring consecutively, the green (measured from the excitable side) and the red (measured from the non-excitable side) curves are the averages of these signals.

For the spontaneous activity measurements, each AP was detected by a 40 μV threshold from heart muscle side. These APs were then plotted for both heart muscle and fibroblast sides since the measurements are simultaneous (FIG. 15b, top). The magnitude of the electrical signal decreased upon passing to the fibroblast side and attenuated over distance whereas heart muscle side did not show any attenuation in the signal (FIG. 15b, top).

Next, we applied electrical stimulations from both excitable (FIG. 15b, middle) and non-excitable (FIG. 15b, bottom) sides and measured the electrical response and signal propagation throughout the culture. For these stimulation measurements, the signals collected were plotted using the stimulation instant (precisely defined by the input signal) as t=1 μs for each stimulation (FIG. 15b, middle and bottom). Since the heart muscle cells exhibit spontaneous beating that results in membrane potential changes, to show signal propagation, we stimulated the cells with a higher frequency than their spontaneous electrical activity and used the change in the frequency of the membrane potential to assess the signal propagation.

Heart muscle cells can be stimulated electrically, and can actively generate a propagating AP through their voltage-sensitive ion channels upon an external electrical stimulation. In addition, they can propagate an input signal via their cell-cell connections (i.e. gap junctions). Therefore, in the forward direction (heart muscle to fibroblast, FIG. 15b, middle), upon stimulation from the excitable side of the culture, the heart cells paced their beating rate to the stimulation frequency, and passed the high frequency signal to the fibroblasts, where we were able to read the output signal. Fibroblasts, on the other hand, are non-excitable cells that do not produce APs, as they lack the abundance of the type of membrane-bound ion channels that render a cell excitable. In other words, these non-excitable cells cannot propagate a signal coming directly to their membrane from an external source, but they can couple with neighboring cells through cell-cell junctions and can thus passively relay electrical signals up to a certain distance via gap junctions. As a result, in the reverse direction (fibroblast to heart muscle, FIG. 15b, bottom) they did not show any response upon stimulation. This data demonstrates that the fibroblasts were able to relay passively the signals coming through gap junctions whereas they were not able to propagate any signals they received directly as external stimulation. This unidirectional signal propagation, is in agreement with our computer simulations that we have included in the last year's progress report, and shows the diode-like nature of heart muscle-fibroblast interactions, which inspired the MCD design.

Example 16

Muscle-Cell Based Diode (MCD)

Figure 16:
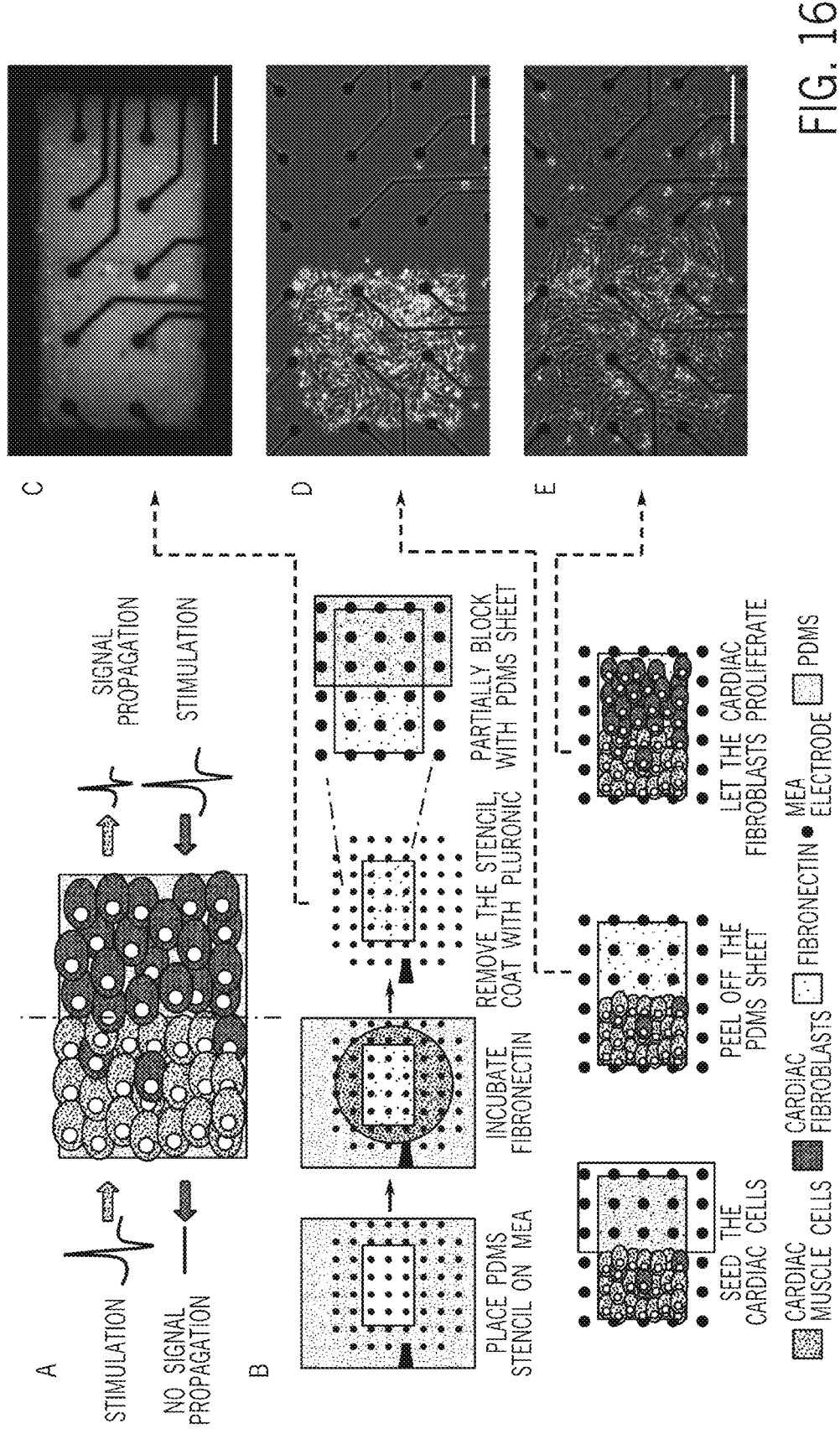
FIG. 16. MCD design and working principle showing the unidirectional signal propagation (a). Schematic of the co-culture patterning approach to create MCDs on MEAs (b). Fibronectin pattern on the MEA substrate visualized using Alexa-488 tagged fibrinogen (c). Cardiac muscle (CM) enriched cell pattern after the removal of PDMS sheet covering half of the pattern (Day 1, d). Completed MCD structure consisting of CM cells and CFs (Day 6, e). (Scale bars: 200 μm).

A modular circuit component, the MCD, was designed, where electrically excitable CM and non-excitable CF cells are confined in rectangular micropatterns (FIG. 16a). Achieving such a confined pattern is necessary to isolate this circuit component from signals coming from elsewhere to minimize the error and noise. In order to achieve the isolated components, the first step is to precisely control the distribution of CMs and CFs. However, this is a very challenging task. Current co-culture patterning approaches either confine only one cell type or use sophisticated automated printing methods. Furthermore, these methods require a second cell seeding procedure, which causes stress for the first seeded cells and potential cross contamination (one cell type attaching on the other). In the disclosed MCD design it is crucial to avoid the presence of excitable CM cells in the CF side, since they would render the non-excitable region excitable.

To generate these defined co-cultures of CM cells and CFs in rectangular patterns of 500×1000 μm stencil based protein patterning and partial covering of the protein pattern temporarily was used in combination with a self-forming micropatterning approach (FIG. 16b). Specifically, substrate surfaces were selectively functionalized by fibronectin adsorption for preferential cell attachment using a micropatterned PDMS stencil having 500×1000 μm rectangular openings (FIG. 16c). To minimize cell attachment and/or growth outside the protein pattern, the substrate surface was treated with an anti-fouling agent (Pluronic F127), and the media was depleted of residual fibronectin prior to cell seeding. A PDMS sheet was then used to partially block the fibronectin pattern in order to populate these micropatterned surfaces with the two different cell types in a controlled manner. After the seeding of the cardiac cell suspension containing 19%±1 CFs and 81%±1 CM cells (n=3), the PDMS was removed (FIG. 16d). In addition to differential excitability of CMs and CFs, these two cell types are also different in terms of their proliferative behavior. Unlike CMs, CFs are highly proliferative. Therefore, cells proliferating across the pattern (FIG. 16e) are expected to be only CFs resulting in a purely non-excitable cell population on one end of the MCD. This self-forming patterning approach ensures that there are no excitable cells on the non-excitable end.

Example 17

Diode Function of the MCD

Figure 17:
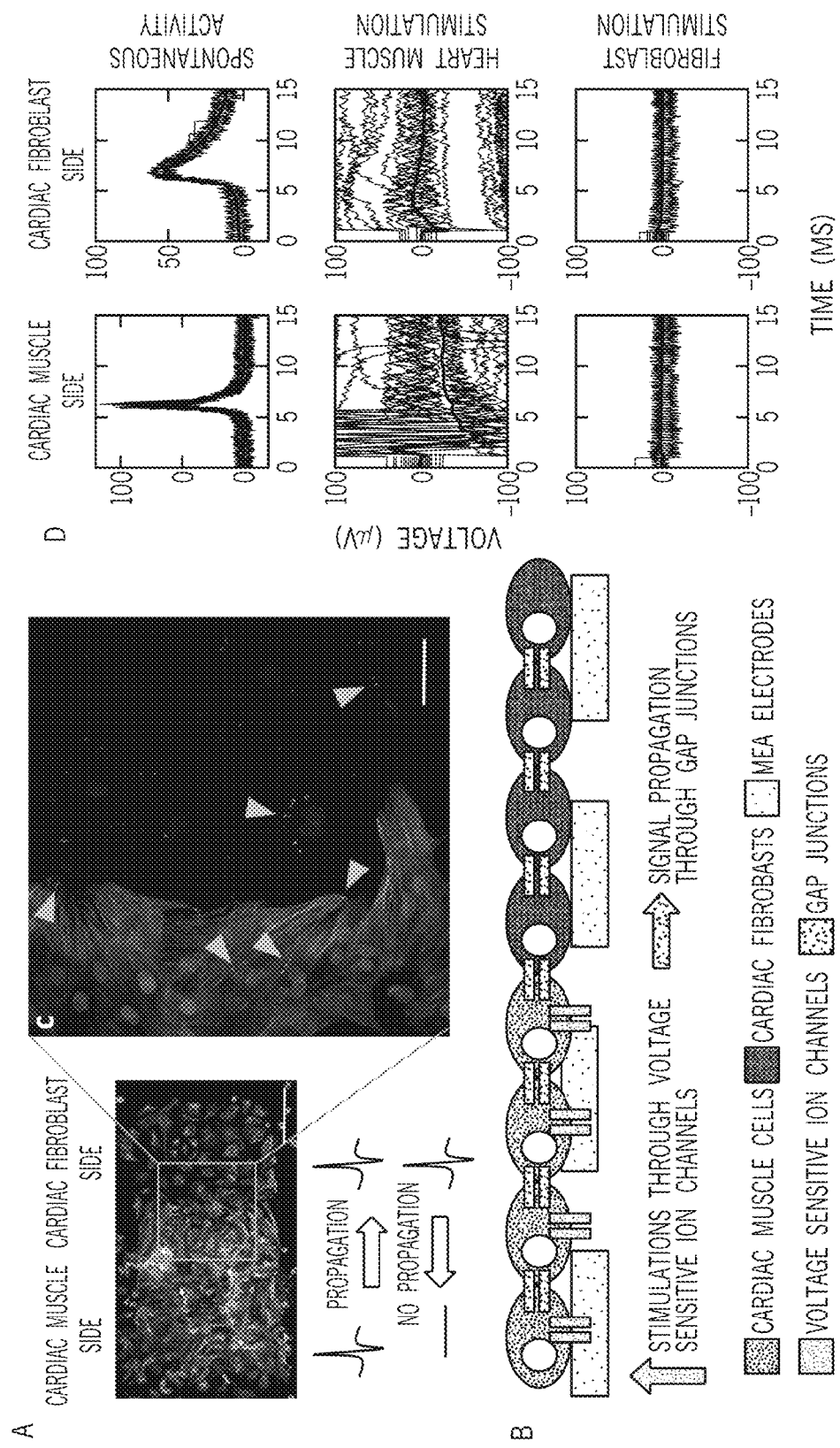
FIG. 17. Fluorescence image of Troponin-I (green) and Vimentin (red) immunostaining of the MCD counter stained for the cell nuclei (blue) (a). Working mechanism of the MCD (b). Fluorescence image of Troponin-I (green) and Connexin 43 (red) immunostaining of the MCD counter stained for the cell nuclei (blue) (c, scale bar: 100 μm). Electrical activity of the MCD (d) measured from CM side (left) and CF side (right) for samples with spontaneously beating cells (d, top) and for samples stimulated from the CM side (d, middle) and the CF side (d, bottom) sequentially.

Once the MCD was obtained through CF proliferation, we performed double immunostaining on Day 6 (FIG. 17a) to examine the distributions of the micropatterned cell populations. FIG. 17 shows Vimentin (CF marker) and Cardiac Troponin-I (CM marker) staining of the MCDs. Immunostaining data confirmed that there were no CM cells on the CF side of the pattern and that CFs were able to proliferate towards the protein side and complete the structure as expected. Therefore, our self-forming micropatterning approach was successfully implemented.

Various ion channels contribute to the excitability of CM cells. However, CFs do not have the same type, distribution and density of such channels, and thus cannot fire APs upon an input. For example, unless genetically modified, CFs lack most of the voltage sensitive K+channels, which is crucial for excitability. Stimulations from CM side are received through these voltage sensitive ion channels and APs are propagated through gap junctions (FIG. 17b). FIG. 17c shows, nuclei (blue) of both CM and CF cells, striated CM cells (green), and the gap junctions (red) between CM-CM, CM-CF and CF-CF, which are crucial for intercellular ion transportation.

FIG. 17d shows membrane potential measurements on MCDs using the MEAs. Throughout these measurements we monitored the MCD to confirm the presence of healthy, beating cardiac cells on the excitable half of the MCD. We measured the spontaneous membrane potentials of the cells of the MCD to be lower than that of the cells in the unconfined, patterned co-culture for both CM and CM cells (FIG. 17d, top). However, this voltage was sufficient to illustrate unidirectional signal propagation through the MCD. In future studies, to improve electrical activity of the micropatterned cells, the protein pattern could be modified to provide an anisotropic alignment to seeded cells. Similar to previous measurements with unconfined, micropatterned co-culture, we stimulated and measured the MCD from both CM and CF cell ends. In the forward direction, upon electrical input using the MEAs, the CM cells were excited and the signals propagating through these gap junctions were measured from the CF side (FIG. 17d, middle). In the reverse direction, the CF cells cannot be excited upon the same magnitude of electrical stimulation since they lack the proper ion channels on their membranes, thus the signal cannot be amplified and propagated, and there was no detectable output signal (FIG. 17d, bottom). These results showed that the MCD successfully operates as a diode by propagating the applied signal unidirectionally, and that the cells preserved their transport properties even under confinement.

Example 18

Logic Gate Design

MCD developed in this study pave the way for cell-based logic gates, with an ultimate goal of creating cell-based biocomputing networks that can be used for interfacing living tissue with traditionally manufactured electronic and mechanical devices or as control units for biosensors or artificial bioactuator-based systems. As a first step towards this aim, we have designed a logic gate where one can obtain 'OR' or "AND" gate functions depending on the thickness of the non-excitable cell connector in the device design (FIG. 18a). In this configuration the thickness t of the fibroblast insert in the pattern creates a threshold effect. When this thickness is thin one input will be enough to be propagated to the fibroblast end, essentially achieving an 'OR' gate. With increased thickness, the signal from input is diminished faster. In this case the input signal can not reach the output unless it is strong enough. This operation requires both inputs to be simultaneously paced to pass the information to output and thus, constitute an 'AND' gate. Truth tables of these gates can be represented with 'paced' and 'not paced' for binary operations '1' and '0', respectively (Table 1). Critical thickness for this kind of threshold effect can be found by sweeping the thickness t for the fibroblast insert. To this end we will control the PDMS sheet thickness using soft lithography techniques.

TABLE 1

Truth tables of the "OR" and "AND" gate designs

| Input 1 | Input 2 | 'OR' gate Output | 'AND' gate Output |
|---------|---------|------------------|-------------------|
| Paced | Paced | Paced | Paced |
| Paced | Not Paced | Paced | Not Paced |
| Not Paced | Paced | Paced | Not Paced |
| Not Paced | Not Paced | Not Paced | Not Paced |

The heart muscle cells are physiologically different from the fibroblasts. These differences include different type and extent of ion channels, as well as different membrane potentials. Cardiac fibroblasts are less polarized (−20 to −40 mV) than the heart muscle cells (−60 to −80 mV). In the 'OR' and 'AND' gate designs we propose to read the output from the fibroblasts. To amplify this output signal, a heart muscle cell amplifier can be used at the output (FIG. 2.3.1b), amplifying the output signal while passing the signal from fibroblasts. Therefore, adding the amplifier at the output will not affect the operation of the logic gates.

Previously, rat hippocampal neurons were used to create logic gates.[12] Above a certain critical density, neuron networks fire signal bursts both spontaneously and upon electrical stimulation. By confining these cells to defined geometries, it was possible to create threshold components, which were demonstrated to show nonlinear input/output characteristics and eventually function as logic gates. In order to attain an 'AND' gate functionality, one of the arms of the cell pattern had to be treated using a Calcium ($Ca^{2+}$) channel blocker to impede the signal. On the other hand, the logic gates we introduced in this study can be used for cell-based information processing without the need for blockers, other chemicals, or altering the gene expression of the cells.

Example 19

Electrical Properties of Human Induced Pluripotent Stem Cell (hiPSC)-Derived Cardiomyocytes (iCMs)

Figure 19:
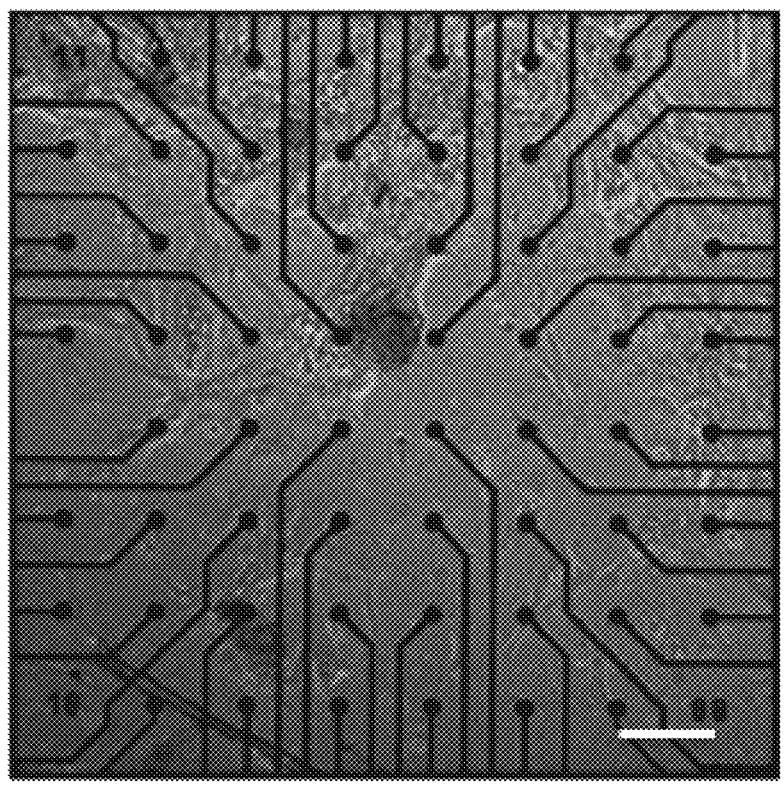
FIG. 19. iCM cells seeded on MEAs. (Scale bar=200 μm)
Figure 20:
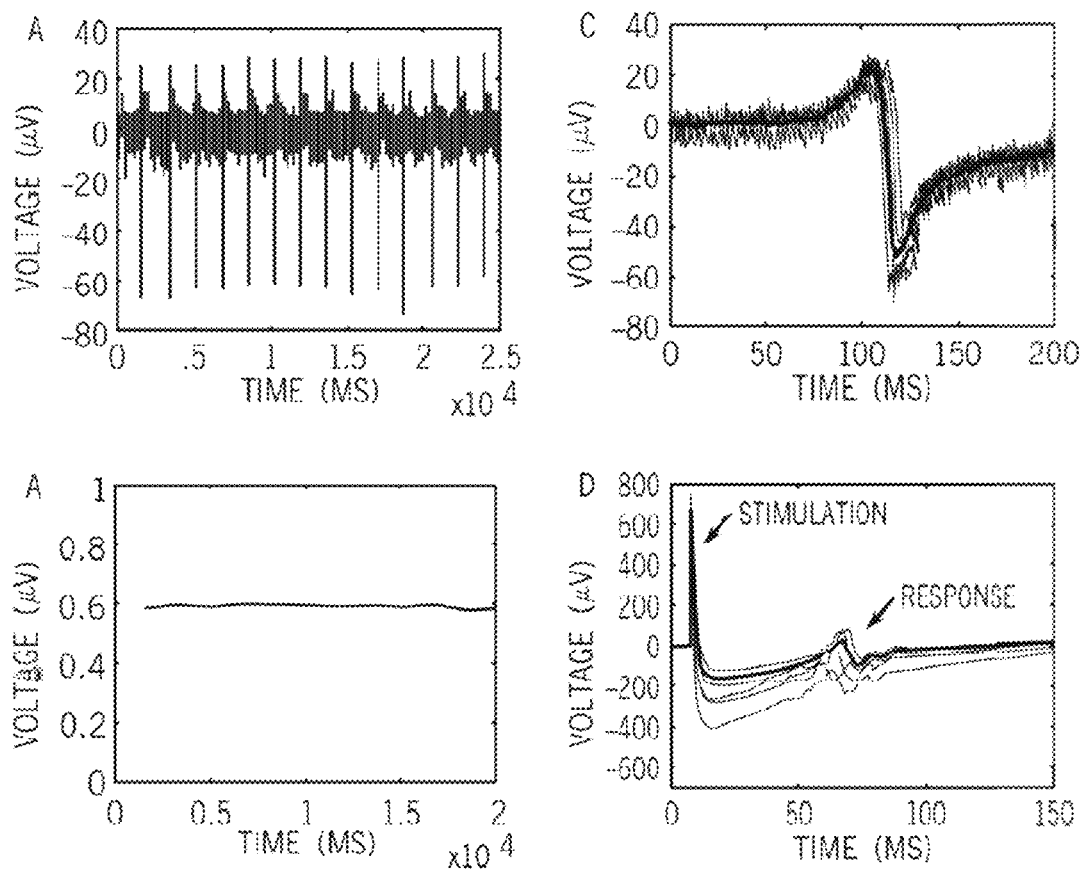
FIG. 20. Electrical characterization of iPSC-CMs. Spontaneous electrical activity (a), frequency (b), single AP form (c) and stimulation graphs (d).

The use of stem cells allows for an inexhaustible source of cardiomyocytes from various species, each with its own given set of characteristics, that can additionally be genetically modified to provide parameters that are not easily attainable using primary cells such as modified surface receptors or membrane channels. As such, in our future studies we are aiming to replace the neonatal heart muscle cells with iCMs. This would also minimize the requirement for primary animal tissues for fabrication of cell-based circuit components. In addition, human iPSC derived CMs can be used for patient specific man-machine interface applications. To this end, iCM differentiation induction was adapted from a previously established protocol. Briefly, on day 1 of differentiation, hiPSCs were treated with RPMI Medium 1640 supplemented with B27 without insulin (2%), beta-mercaptoethanol (3.4E-4%) and P/S (1%) (CM(−) media) with the addition of glycogen synthase kinase 3 beta inhibitor (CHIR) (10 µM). Twenty-four hours after (day 2), hiPSCs were treated with CM(−). On day 4, CM(−) media supplemented with IWP (10 µM) was added. On day 6, medium was changed to CM(−). On day 9, medium was changed to RPMI Medium 1640 supplemented with B27 (2%), beta-mercaptoethanol (3.4E-4%), and P/S (1%) (CM+). From day 9-on media was changed every 3 days and beating was observed as early as day 12 and routinely by day 21 of differentiation. On day 21, iCMs were trypsinized and seeded onto a fibronectin coated (50 µg/mL) MEA and supplemented with DMEM complete (10% FBS, 1% P/S) with media changes every third day until the recommencement of beating. Once beating recommenced, electrical membrane potential from the electrodes were measured using MEAs (FIG. 19). Spontaneous activity was measured (FIG. 20a) and frequency analysis (FIG. 20b) was performed using MATLAB. Single APs were plotted together and averaged as gray and black, respectively (FIG. 20c). Finally, we have successfully stimulated these cells at 0.5 Hz (FIG. 20d). Through the analysis of the spontaneous and stimulated electrical signal propagation, we found that the conduction velocity from these measurements to be 4.6 cm/s which was comparable to previous literature.

Example 20

Protein Micropattern Fabrication

We used micropatterning techniques to confine CMs and CFs within specific geometries. The major challenge in developing this CM-CF co-culture system is caused by the unique characteristics of each cell type. The CFs are highly proliferative, while the CMs are not and are comparatively less robust. Hence we optimized substrate treatment and culture techniques to control the proliferation and non-specific attachment of CFs as explained in the following sections.

Figure 21:
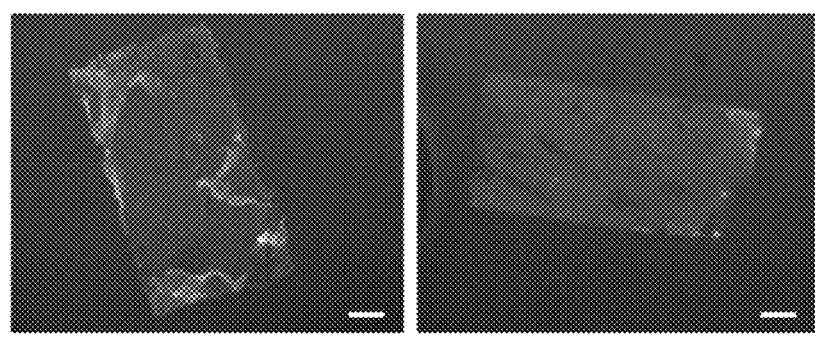
FIG. 21. Microcontact printed fibronectin protein patterns on silane treated substrate (scale bars: 100 μm).

Dichlorodimethylsilane was chosen to achieve a contact angle of 97°-105°, which was shown to be favorable for adhesion of both fibronectin and Pluronic F127[4]. Silane coating was achieved through vacuum evaporation after the substrates were cleaned with 70% methanol and Piranha (1:3 $H_2O_2:H_2SO_4$). However, through this technique, the protein transfer onto the substrate was not uniform and the efficiency of successful transfer was low (FIG. 21).

Figure 22:
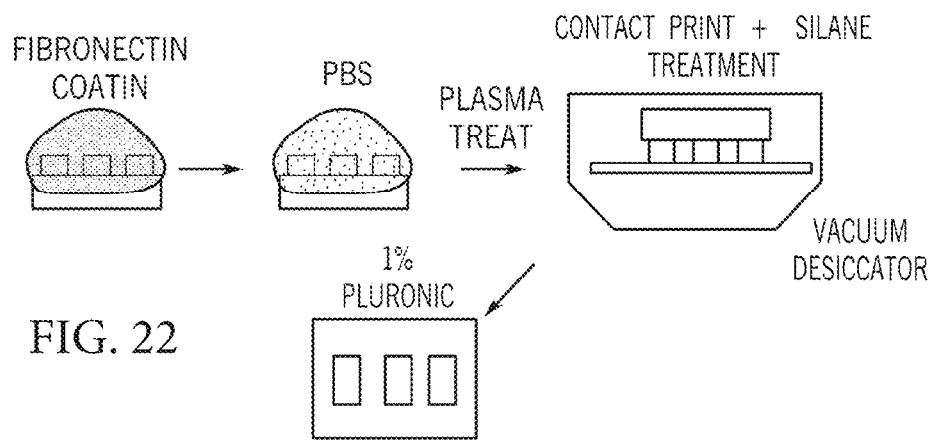
FIG. 22. Schematic representation of simultaneous process of microcontact printing and silane coating.

Therefore, we tested a new method of patterning, where the contact printing of proteins and silane coating is carried out simultaneously in the vacuum chamber. Briefly, substrates were washed three times with methanol and isopropyl alcohol (IPA), and then rinsed with deionized (DI) water. The substrates were then left to air dry and treated with air plasma for 1 min. Meanwhile, microcontact printing stamps were incubated with protein for 1 hour, the fibronectin solution was removed gently, and the surface washed with phosphate buffer solution (PBS). Then the surface is briefly dried with air and brought into conformal contact onto the cleaned substrates. Protein incubated stamp was placed on the substrate and then together they were placed in the vacuum desiccator for silane treatment. Silane deposition is then carried out for 30 min, after which the sample was gently removed from the vacuum chamber and place in 2% Pluronic solution for 1 hr. The substrate was then washed and kept in PBS until cell seeding. The principle behind this technique is that the patterned protrusion on the stamp is the only surface that would come in contact with the substrate and form the conformal contact for the protein transfer, while the silane vapor can be deposited on to the remaining areas on the substrate. The schematic of the process is shown in FIG. 22.

Figure 23:
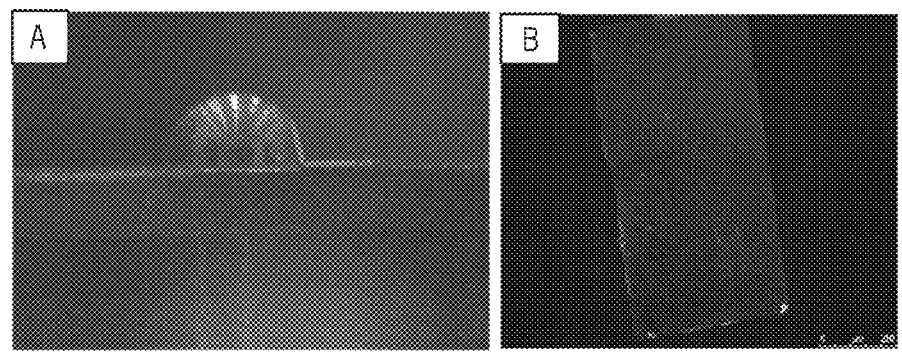
FIG. 23. (A) Sample measurement of contact angle of silane coated substrate using the simultaneous microcontact printing and silane deposition approach, and (B) the obtained fibronectin pattern using this approach.

Contact angle measurement was performed to confirm the hydrophobicity of the surface (FIG. 23A). Through this approach, the protein transfer was more uniform (FIG. 23B) compared to the method described above (FIG. 21).

Example 21

Cell Seeding and Optimizing the Culture Conditions

Figure 24:
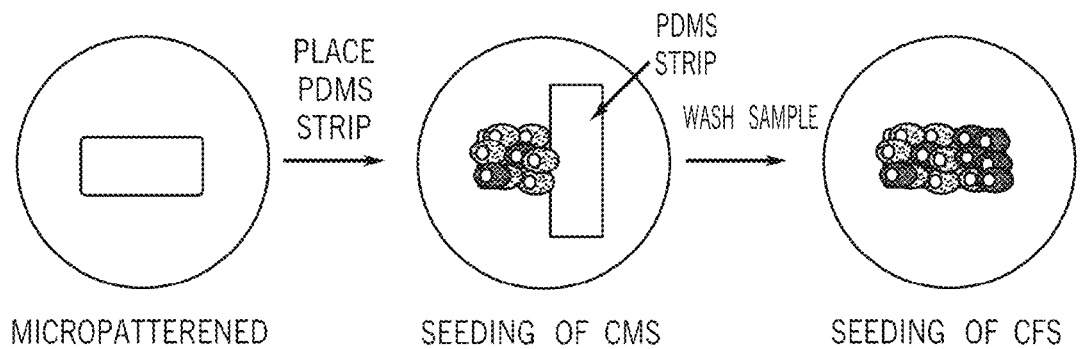
FIG. 24. Schematics of the sequential double cell seeding.
Figure 25:
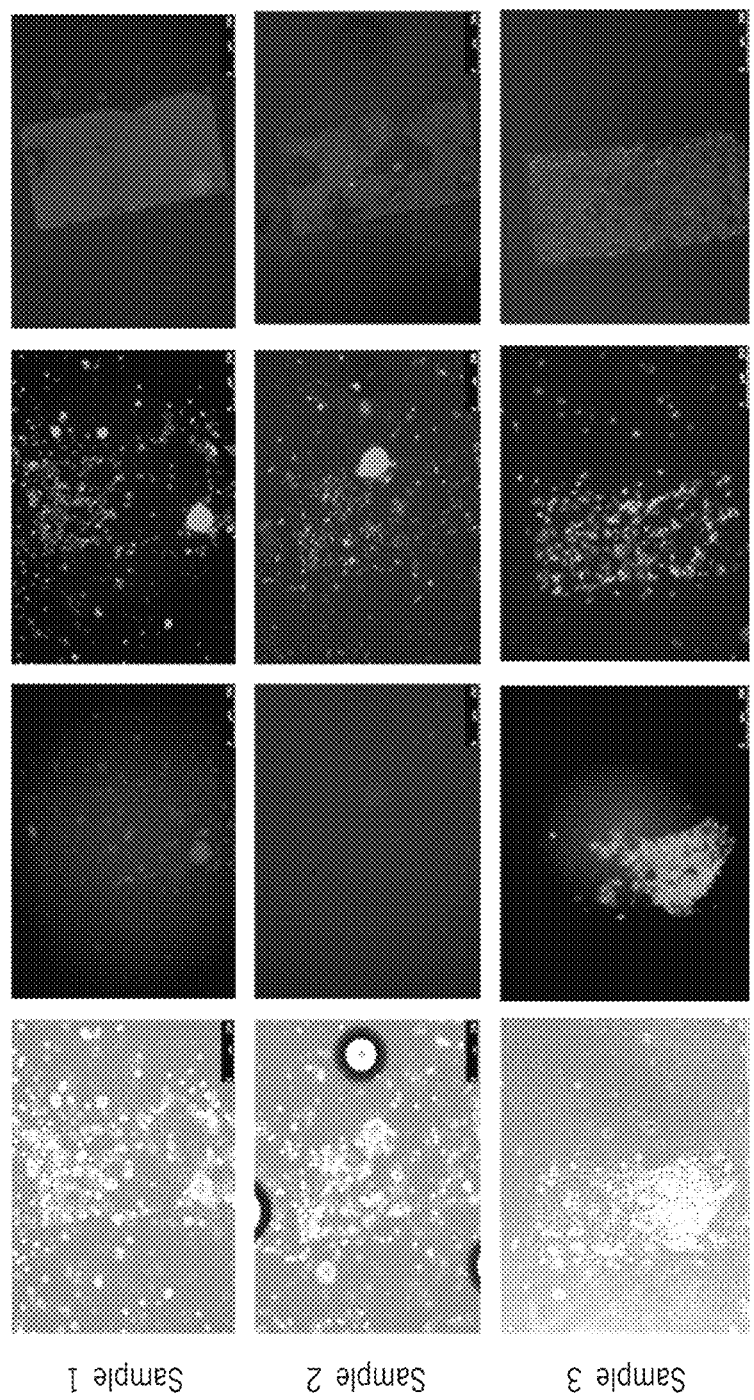
FIG. 25. CF-CF double seeding trials. The first seeded cells were stained with blue cell tracker and second seeded cells were stained with red cell tracker.

Protein micropatterns obtained using the simultaneous microcontact printing and silane deposition approach described above, were partially covered with a polydimethylsiloxane (PDMS) strip prior to cell seeding. The first cell type, the CMs, were seeded and incubated for 24 hours to ensure confluent CM attachment. The unattached CMs were then washed and maintained in culture media for 2 days after which the second cell type, the CFs, were seeded and washed after 45 minutes incubation (FIG. 24). Prior to CM-CF seeding experiments, to optimize the seeding conditions, CF-CF double seeding trials were carried out (FIG. 25). In order to minimize unwanted cell attachment and growth, both cells were seeded and maintained in Dulbecco's Modified Eagle's Media (DMEM) supplemented with 10% fibronectin-depleted serum. Using fibronectin-depleted serum containing media has reduced random attachment of cells during the second seeding.

Figure 26:
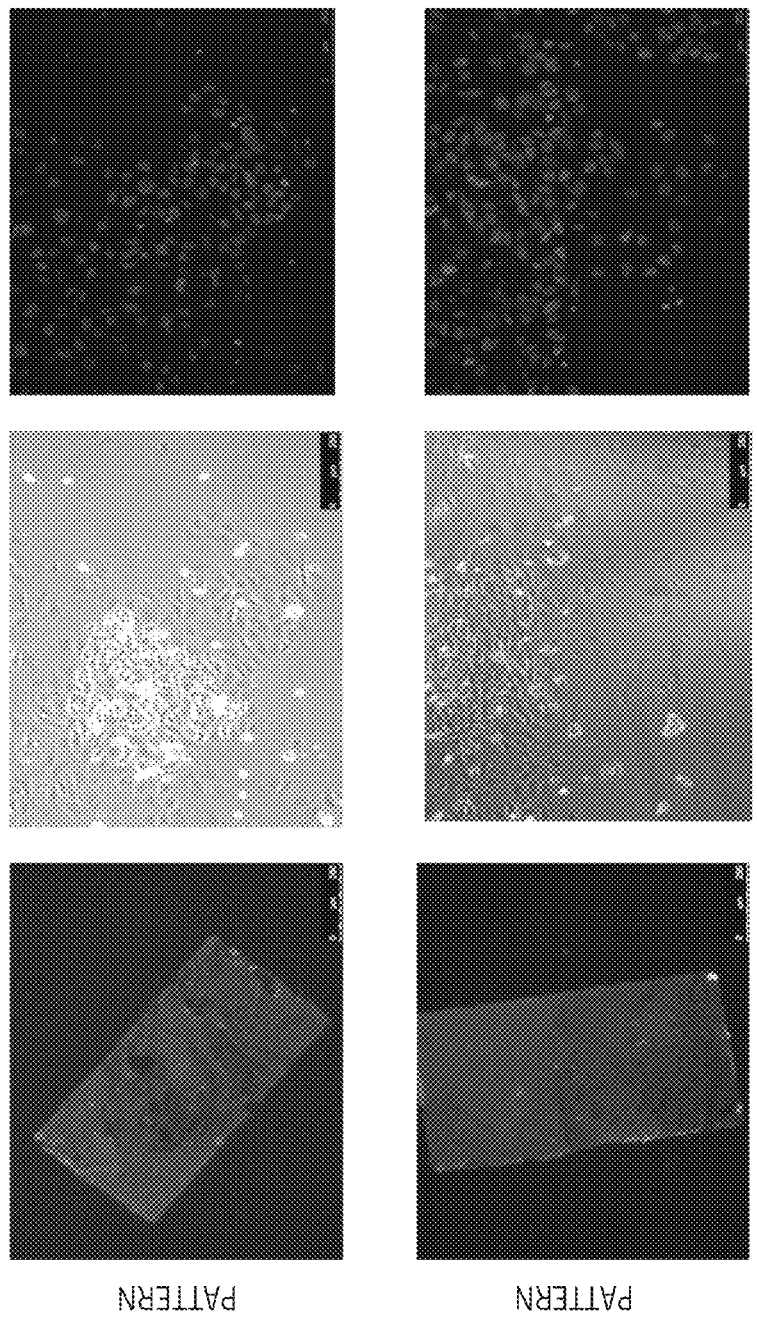
FIG. 26. Random attachment of CFs (stained with red cell tracker) on the substrates and on CMs (stained with blue cell tracker).

As can be seen from the three independent samples shown in FIG. 25, only one of the samples (sample 3) resulted in acceptable success in terms of cellular confinement and localization. In the other two samples (sample 1 and 2), the first seeded cells shrunk or detached after the second seeding. When this trial was repeated with CMs and CFs, we observed random attachment of CFs especially on the area not initially covered by the PDMS strip despite using the fibronectin-depleted serum (FIG. 26). This could be because, in case of CM-CF co culture, the second seeding is carried out two days after the first cell type (i.e. CMs) had been seeded and confluently adhered. In the meantime, the PDMS sheet was kept on the substrate and removed only before the seeding. Hence, we observed non-specific attachment predominantly on the side of CMs, which was exposed to culture media as compared to the half covered by the PDMS strip. In case of CF-CF co culture, we do not observe this because the incubation period for CF adhesion is shorter (45 minutes). Furthermore, the second seeded cells almost always attached on top of the first seeded ones, either causing detachment of the CMs or interfering with their contractile properties.

Example 22

Stencil Based Micropatterning-Self Proliferation of CFs

Figure 27:
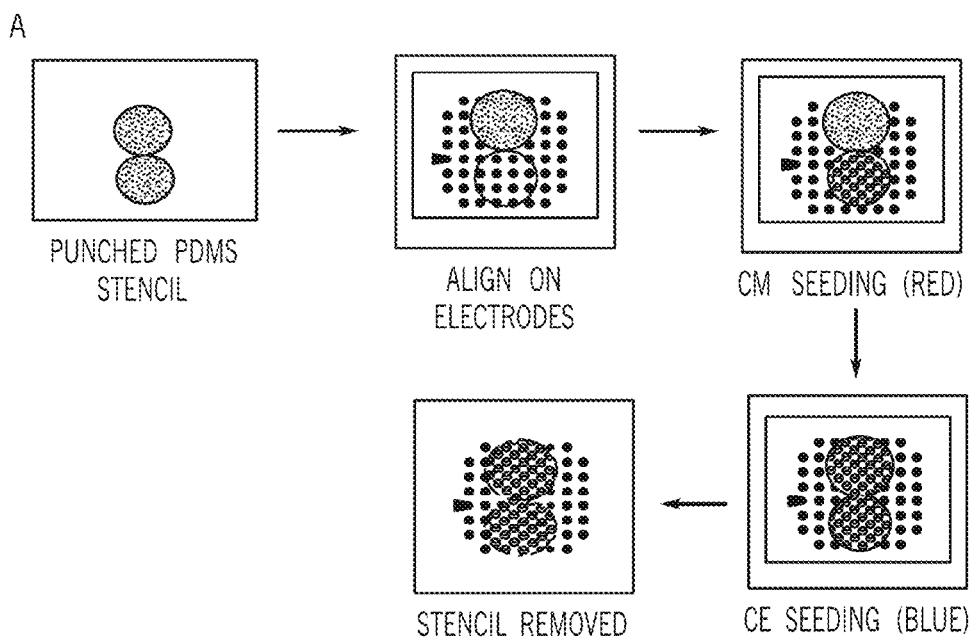
FIG. 27. Schematic representation of stencil based patterning (A). Bright field images showing seeded CMs, CFs and proliferation across the gap over time in two samples (B).
Figure 27:
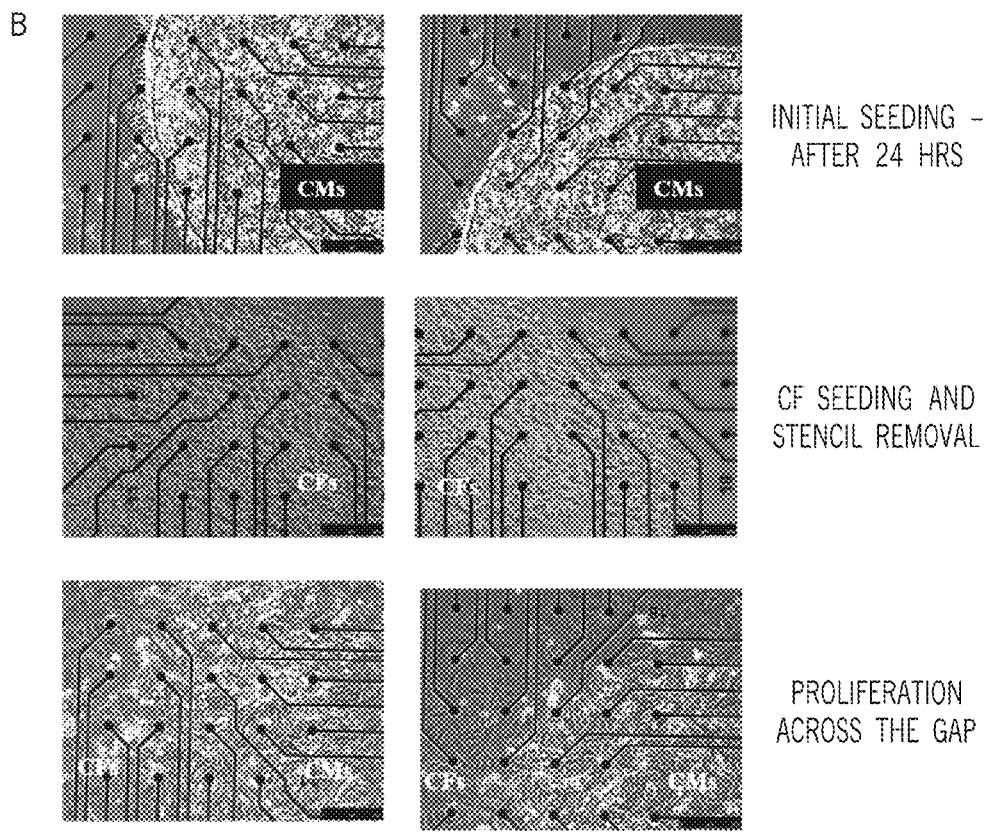

We used thin PDMS stencils where we punched out two small holes in close proximity to each other on a thin PDMS film (FIG. 27A). First punched PDMS was removed and CMs were seeded at a density 100,000 cells/50 µl. Then second punched PDMS was removed and CFs were seeded at the same density. This approach allows keeping cell suspensions of CMs and CFs during the seeding steps separate, and helps prevent cross contamination (CMs attaching on CF side or vice versa). For that purpose, a narrow gap between two holes works as a barrier during the seeding process. Once the CFs attached, the sample was washed and the PDMS stencil was completely removed to allow the CFs to proliferate and bridge the gap, forming connections with the CMs (FIG. 27B).

Thus, using this patterning approach we successfully obtained CF-CM co culture without non-specific attachment of CFs. However, there were some drawbacks. This approach does not allow us to control the pattern shape and size precisely. Furthermore, keeping two droplets of cell suspension without contacting one another was challenging.

Example 23

Micropatterning Stencils

Figure 28:
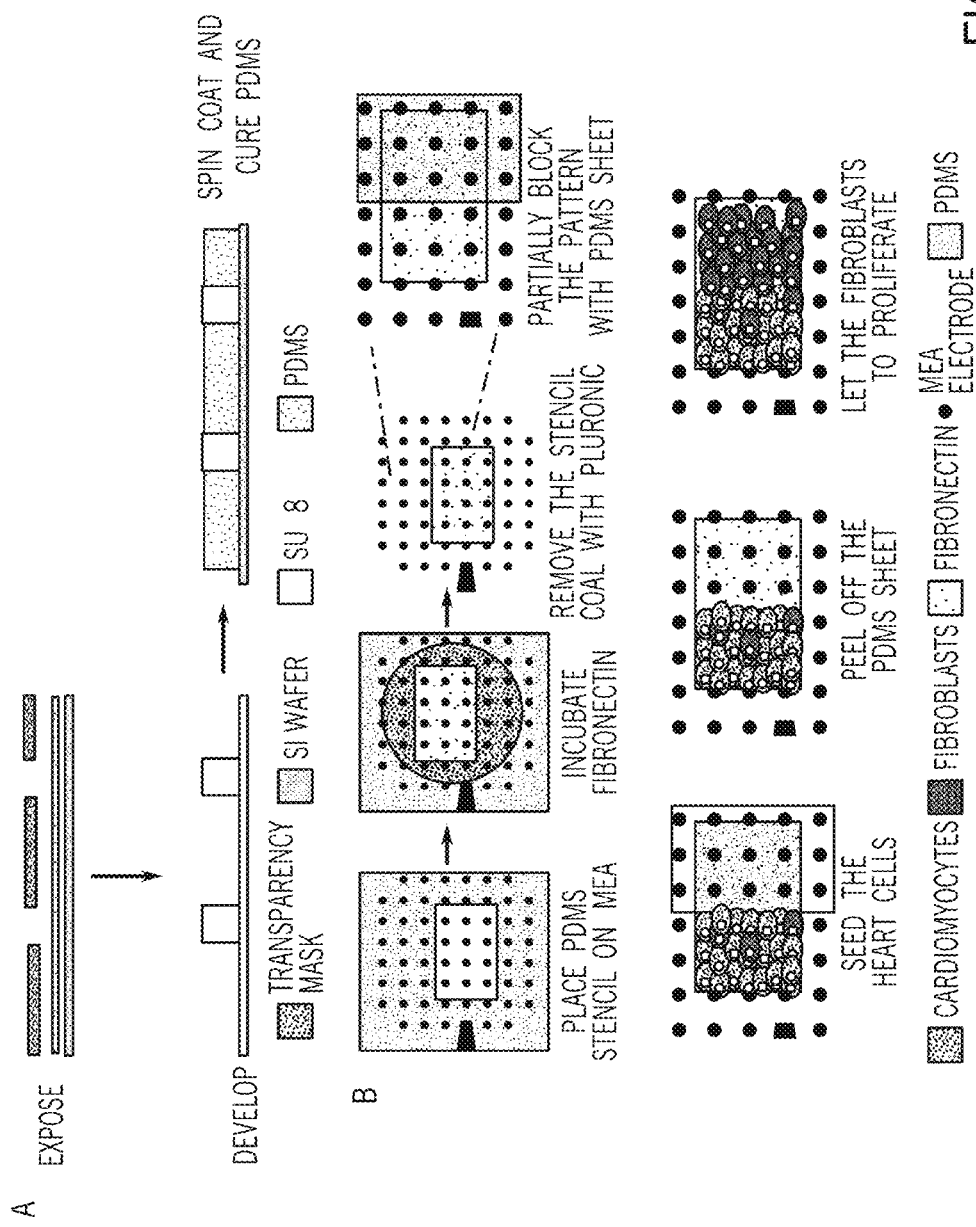
FIG. 28. Schematic of fabrication of PDMS thin film stencil (A) and the co-culture patterning approach to create patterned CFs and CMs on MEAs (B).

To control the pattern size and shape, we have used soft lithography techniques[5] and fabricated micropatterned stencils (FIG. 28A). Briefly, SU-8 2075 (MicroChem Corp., USA) photoresist was spin coated (1000 rpm, 300 rpm/s, 30 s) to obtain a thickness of 200±20 µm on a silicon (Si) wafer (University Wafer). Si wafer was then soft baked for 10 minutes at 65° C. and 45 minutes at 95° C. followed by the UV exposure through a transparency mask (Advanced Reproductions) using a mask aligner (Karl Suss MJB-3), and then was developed using SU8 developer (MicroChem Corp.). PDMS (Ellsworth Adhesives) base and curing agent were mixed in 5:1 ratio, degassed, spin coated on the silicon wafers (750 rpm, 100 rpm/s, 30 s), and cured at 70° C. for 30 minutes. Finally, the thin film PDMS was carefully peeled off to obtain the elastomeric stencils with the desired patterns and sterilized under UV prior to cell culture use.

Figure 29:
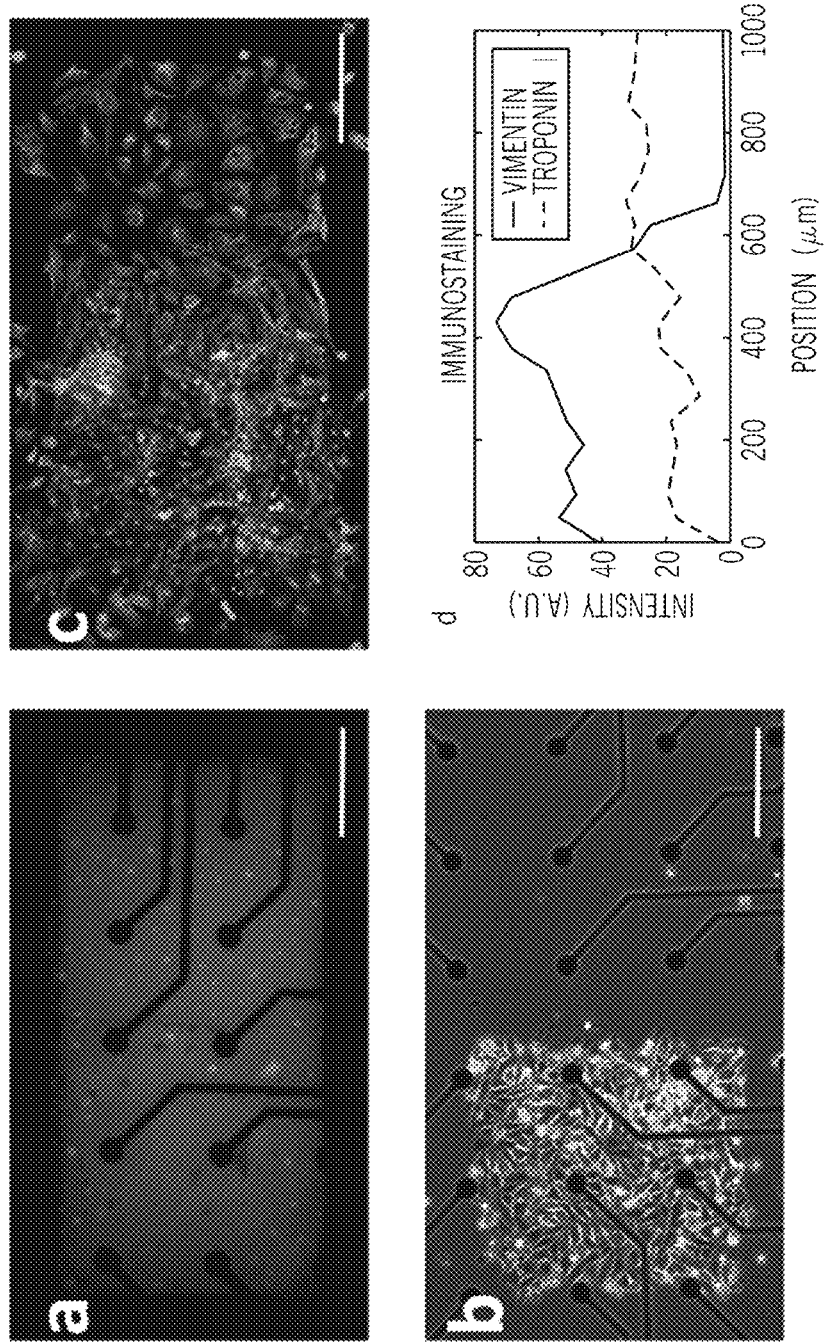
FIG. 29. Fibronectin pattern on the MEA substrate visualized using Alexa-488 tagged fibrinogen (a). CM enriched cell pattern after the removal of PDMS sheet covering half of the pattern (Day 1, b). Fluorescence image of Troponin-I (green), Vimentin (red) and nuclei (blue) immunostaining (Day 6, c). Intensity analysis of the immunostaining (d) showing the lack of CMs on the right side of the MCD (scale bars: 200 μm).

In our muscle cell-based diode (MCD) design it is crucial to avoid the presence of CMs in the CF side, since they would render the non-excitable region excitable. To generate precisely defined co-cultures of CMs and CFs in rectangular patterns of 500×1000 µm we used stencil based protein patterning[6] and partial covering of the protein pattern temporarily[7] in combination with our self-forming micropatterning approach (FIG. 28B). Specifically, substrate surfaces were selectively functionalized by fibronectin adsorption for preferential cell attachment using a micropatterned PDMS stencil having 500×1000 µm rectangular openings (FIG. 29a). To minimize cell attachment and/or growth outside the protein pattern, the substrate surface was treated with an anti-fouling agent (Pluronic F127), and the media was depleted of residual fibronectin prior to cell seeding. A PDMS sheet was then used to partially block the fibronectin pattern in order to populate these micropatterned surfaces with the two different cell types in a controlled manner. After the seeding of the cardiac cell suspension containing 19%±1 CFs and 81%±1 CM cells (for details of the cell isolation protocol, please see last year's report), the PDMS was removed (FIG. 29b). In addition to differential excitability of CMs and CFs, these two cell types are also different in terms of their proliferative behavior. Unlike CMs, CFs are highly proliferative. Therefore, cells proliferating across the pattern are expected to be only CFs resulting in a purely non-excitable cell population on one end of the pattern. This self-forming patterning approach ensures that there are no excitable cells on the non-excitable end.

Once the co-culture pattern was obtained through CF proliferation, we performed double immunostaining on Day 6 to examine the distributions of the micropatterned cell populations. FIG. 29c,d shows Vimentin (CF marker) and Cardiac Troponin-I (CM marker) staining of the MCDs. Immunostaining data confirmed that there were no CMs on the CF side of the pattern and that CFs were able to proliferate towards the protein side and complete the structure as expected. Therefore, our self-forming micropatterning approach was successfully implemented.

Example 24

Hydrophobicity of MEA Substrate Surfaces

Although the patterning process is the same for all substrates, we observed that the hydrophobicity of the substrate plays a determining role in the adsorption of the protein. When the surface is too hydrophobic the protein does not get adsorbed or detaches over time (FIG. 1.2.5). However, if the surface is not hydrophobic enough, CFs attach and/or proliferate outside the pattern area (FIG. 1.2.6). Therefore, to obtain confined patterned co-culture structures, it is crucial to control the surface properties precisely. The described method above is optimized to work best on MEA substrate surfaces, so the inherent hydrophobicity of the MEA substrates gives the best results. However as the MEA substrates are reused in culture, they become more hydrophilic due to constant exposure to culture media. As such, to improve the efficiency and reduce the cost through multiple usages of the MEA substrates, we are aiming to standardize the surface properties of the MEA substrates, regardless of how many times they are being used in culture, through surface modifications.

We have investigated the surface properties of different substrates to understand the variation in the outcome of our protein and cell patterning process. Brand new MEAs are hydrophobic, with contact angles comparable to that of silane coated substrates. However, the surface properties of these MEAs change with repeated use and they could vary between used and new MEAs (FIG. 1.2.7, left and right, respectively). From these measurements we have concluded that contact angle of 82° was ideal whereas 95° was too hydrophobic and 46° was too hydrophilic. Our next step is to treat the surfaces of the used MEAs to keep the surface properties closer to that of a new MEA.

Example 25

Contractility Across CM-CF Boundary

Silanized glass coverslips were coated with fibronectin as a single droplet, followed by a PBS wash and 1% Pluronic F-127 treatment for 1 hour. After that thin PDMS membranes were cut manually into narrow (300-500 µm width) and wide (~1000-1600 µm width) strips and placed at the center of the fibronectin-coated substrate. The CM-CF (4:1) cell suspension was then seeded onto the substrate (with a cell density of 500,000 cells/ml), and left undisturbed for 24 hours. After the incubation period the samples were washed and the PDMS strip removed to allow the CFs to self-proliferate over time.

After the CFs bridge the gap across the two CM halves, we treated the sample with 5 µM calcium Fluo-4 dye in Tyrodes salt solution, supplemented with 0.2% Pluronic F-127. The samples were incubated for 30 min at 37° C. after which they were washed and re-incubated in fresh DMEM for 30 minutes before imaging. Recording was carried out at 30 fps simultaneously during contractile measurements.

Figure 34:
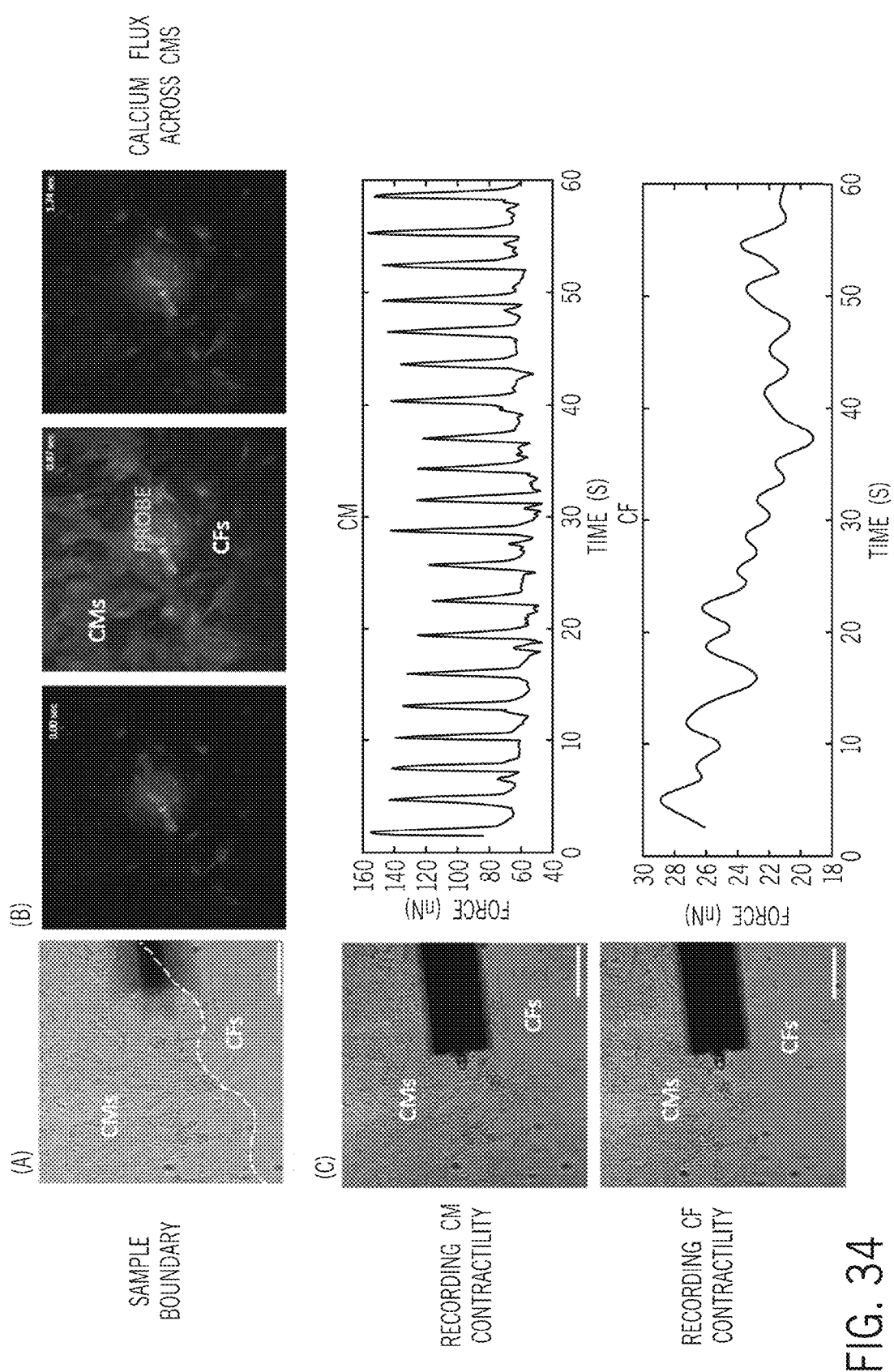
FIG. 34. (a) Brightfield image of CMs-CFs boundary; (b) Screenshots of Calcium flux across CMs; (c) Contractility measurement of CMs (top) and CFs (bottom).

In order to investigate the mechanical signal transduction from CMs to CFs, contractility measurement was conducted at the boundary of CMs-CFs (FIG. 34*a*). In this experiment, a Piuma Chiaro Nanoindenter (Optics11, Amsterdam, The Netherlands) was used to measure the contractility. The probe used had a spring constant and colloidal probe radius of 0.261 N/m and 8 µm, respectively. The target CMs and CFs were chosen according to Calcium flux where the CMs showed visible flux and CFs did not (FIG. 34*b*). The cells were indented with applied force of around 160 nN and 30 nN for CMs and CFs, respectively. The cantilever was kept contact with the cells for 60 seconds to measure the contractility. The beating force magnitude was around 90 nN for CMs and 5 nN for CFs (FIG. 34*c*). The results revealed that CMs contractility can propagate through CFs, and could be detected as an out put from the CF side of the co-culture.

What is claimed is:

1. A diode comprising:
   a group of excitable cells;
   a group of non-excitable cells; and
   a first connector and a second connector, wherein:
   the first connector is electrically connected to the group of excitable cells at a first coupling,
   the second connector is electrically connected to the group of non-excitable cells at a second coupling,
   the group of excitable cells and the group of non-excitable cells are electrically connected at a third coupling, and
   a first number of cells of the group of excitable cells connected to the first connector at the first coupling is greater than a second number of cells of the group of non-excitable cells connected to the second connector at the second coupling.

2. The diode of claim 1, wherein the group of excitable cells comprises at least one cell capable of creating an action potential in response to a signal selected from the group consisting of an electrical signal and a mechanical signal.

3. The diode of claim 1, wherein the group of excitable cells comprises at least one cell selected from the group consisting of neurons, muscle cells, and endocrine cells.

4. The diode of claim 1, wherein the group of excitable cells comprises at least one cardiomyocyte.

5. The diode of claim 1, wherein the group of non-excitable cells comprises at least one cell which is not capable of producing an action potential.

6. The diode of claim 1, wherein the group of non-excitable cells comprises at least one gap junction.

7. The diode of claim 1, wherein the group of non-excitable cells comprises at least one heart fibroblast.

8. The diode of claim 1, wherein:
   a third number of cells of the group of excitable cells connected to the group of non-excitable cells at the third coupling is fewer than the first number of cells connected to the first connector at the first coupling and
   a fourth number of cells of the group of non-excitable cells connected to the group of excitable cells at the third coupling is greater than the second number of cells connected to the second connector at the second coupling.

9. The diode of claim 1, wherein the group of excitable cells and the group of non-excitable cells are configured such that:
   application of a first electrical signal to the first connector causes current to flow from the first connector to the second connector via the group of excitable cells and the group of non-excitable cells and
   application of a second electrical signal to the second connector absent application of the first electrical signal to the first connector does not cause current to flow at the first connector.

10. The diode of claim 1, wherein at the third coupling only a single cell of the group of non-excitable cells is mechanically connected to the group of excitable cells.

11. The diode of claim 1, wherein the group of excitable cells is not directly mechanically or electrically connected to the second connector.

12. A logic gate comprising:
   a first group and a second group of excitable cells;
   a group of non-excitable cells; and
   a first connector and a second connector, wherein:
the first group of excitable cells is electrically connected to the group of non-excitable cells;
the second group of excitable cells is electrically connected to the group of non-excitable cells;
the first connector is electrically connected to the first group of excitable cells;
the second connector is electrically connected to the second group of excitable cells; and
the first group of excitable cells, the second group of excitable cells, and the group of non-excitable cells together form a U shape in which:
a first arm of the U shape comprises the first group of excitable cells,
a second arm of the U shape comprises the second group of excitable cells, and
a base of the U shape comprises the group of non-excitable cells.

13. The logic gate of claim 12, further comprising a third group of excitable cells electrically connected to the group of non-excitable cells.

14. The logic gate of claim 13, further comprising a third connector electrically connected to the third group of excitable cells.

15. The logic gate of claim 14, wherein the first group of excitable cells, the second group of excitable cells, the third group of excitable cells, and the group of non-excitable cells are configured such that the logic gate functions as an OR gate, wherein:
application of a first electrical signal to the first connector and application of a second electrical signal to the second connector at the same time causes current to flow from the first connector and the second connector to the third connector via the first group of excitable cells, the second group of excitable cells, the group of non-excitable cells, and the third group of excitable cells;
application of the first electrical signal to the first connector absent application of the second electrical signal to the second connector causes current to flow from the first connector to the third connector via the first group of excitable cells, the group of non-excitable cells, and the third group of excitable cells;
application of the second electrical signal to the second connector absent application of the first electrical signal to the first connector causes current to flow from the second connector to the third connector via the second group of excitable cells, the group of non-excitable cells, and the third group of excitable cells; and
application of a third electrical signal to the third connector absent application of the first electrical signal to the first connector and absent application of the second electrical signal to the second connector does not cause current to flow at either of the first connector or the second connector.

16. The logic gate of claim 14, wherein the first group of excitable cells, the second group of excitable cells, the third group of excitable cells, and the group of non-excitable cells are configured such that the logic gate functions as an AND gate, wherein:
application of a first electrical signal to the first connector and application of a second electrical signal to the second connector at the same time causes current to flow from the first connector and the second connector to the third connector via the first group of excitable cells, the second group of excitable cells, the group of non-excitable cells, and the third group of excitable cells;
application of the first electrical signal to the first connector absent application of the second electrical signal to the second connector does not cause current to flow at the third connector;
application of the second electrical signal to the second connector absent application of the first electrical signal to the first connector does not cause current to flow at the third connector; and
application of a third electrical signal to the third connector absent application of the first electrical signal to the first connector and absent application of the second electrical signal to the second connector does not cause current to flow at either of the first connector or the second connector.

17. The logic gate of claim 12, wherein each of the first group of excitable cells and second group of excitable cells are capable of creating an action potential.

18. The logic gate of claim 12, wherein each of the first group of excitable cells and second group of excitable cells are capable of creating an action potential in response to a signal selected from the group consisting of an electrical signal and a mechanical signal.

19. The logic gate of claim 12, wherein each of the first group of excitable cells and second group of excitable cells are selected from the group consisting of neurons, muscle cells, and endocrine cells.

20. The logic gate of claim 12, wherein each of the first group of excitable cells and second group of excitable cells are a cardiomyocyte.

21. The logic gate of claim 12, wherein the group of non-excitable cells are not capable of producing an action potential.

22. The logic gate of claim 12, wherein the group of non-excitable cells comprise at least one gap junction.

23. The logic gate of claim 12, wherein the group of non-excitable cells comprise a heart fibroblast.

24. The logic gate of claim 12, further comprising a third connector electrically connected to the group of non-excitable cells.

25. The logic gate of claim 24, wherein the first group of excitable cells, the second group of excitable cells, and the group of non-excitable cells are configured such that the logic gate functions as an OR gate, wherein:
application of a first electrical signal to the first connector and application of a second electrical signal to the second connector at the same time causes current to flow from the first connector and the second connector to the third connector via the first group of excitable cells, the second group of excitable cells, and the group of non-excitable cells;
application of the first electrical signal to the first connector absent application of the second electrical signal to the second connector causes current to flow from the first connector to the third connector via the first group of excitable cells and the group of non-excitable cells;
application of the second electrical signal to the second connector absent application of the first electrical signal to the first connector causes current to flow from the second connector to the third connector via the second group of excitable cells and the group of non-excitable cells; and
application of a third electrical signal to the third connector absent application of the first electrical signal to the first connector and absent application of the second electrical signal to the second connector does not cause current to flow at either of the first connector or the second connector.

26. The logic gate of claim 24, wherein the first group of excitable cells, the second group of excitable cells, and the group of non-excitable cells are configured such that the logic gate functions as an AND gate, wherein:

application of a first electrical signal to the first connector and application of a second electrical signal to the second connector at the same time causes current to flow from the first connector and the second connector to the third connector via the first group of excitable cells, the second group of excitable cells, and the group of non-excitable cells;

application of the first electrical signal to the first connector absent application of the second electrical signal to the second connector does not cause current to flow at the third connector;

application of the second electrical signal to the second connector absent application of the first electrical signal to the first connector does not cause current to flow at the third connector; and application of a third electrical signal to the third connector absent application of the first electrical signal to the first connector and absent application of the second electrical signal to the second connector does not cause current to flow at either of the first connector or the second connector.

27. The logic gate of claim 26, wherein each of the first group of excitable cells and the second group of excitable cells are 100 to 500 micrometers (μm) in width, and further wherein the group of non-excitable cells is 20 to 200 micrometers (μm) in width.

28. The logic gate of claim 12, wherein the first group of excitable cells is not directly mechanically or electrically connected to the second group of excitable cells.

* * * * *